US011825817B2

(12) United States Patent
Kazuki et al.

(10) Patent No.: US 11,825,817 B2
(45) Date of Patent: Nov. 28, 2023

(54) RAT MODEL OF DOWN SYNDROME AND METHOD FOR PRODUCING SAME

(71) Applicants: NATIONAL UNIVERSITY CORPORATION TOTTORI UNIVERSITY, Tottori (JP); TRANS CHROMOSOMICS, INC., Yonago (JP)

(72) Inventors: Yasuhiro Kazuki, Yonago (JP); Mitsuo Oshimura, Yonago (JP)

(73) Assignees: National University Corporation Tottori University, Tottori (JP); Trans Chromosomics, Inc., Tottori (JP)

( * ) Notice: Subject to any disclaimer, the term of this patent is extended or adjusted under 35 U.S.C. 154(b) by 0 days.

(21) Appl. No.: 16/337,381

(22) PCT Filed: Sep. 28, 2017

(86) PCT No.: PCT/JP2017/035236
§ 371 (c)(1),
(2) Date: Mar. 27, 2019

(87) PCT Pub. No.: WO2018/062392
PCT Pub. Date: Apr. 5, 2018

(65) Prior Publication Data
US 2020/0029539 A1    Jan. 30, 2020

(30) Foreign Application Priority Data
Sep. 28, 2016    (JP) .................. 2016-190422

(51) Int. Cl.
*A01K 67/00* (2006.01)
*A01K 67/027* (2006.01)
*C12N 15/02* (2006.01)

(52) U.S. Cl.
CPC ...... *A01K 67/0271* (2013.01); *A01K 67/0278* (2013.01); *C12N 15/02* (2013.01); *A01K 2207/12* (2013.01); *A01K 2207/15* (2013.01); *A01K 2227/105* (2013.01); *A01K 2267/0306* (2013.01)

(58) Field of Classification Search
None
See application file for complete search history.

(56) References Cited

U.S. PATENT DOCUMENTS 6,838,592 B1 *  1/2005  Nixon  .............. A01K 67/0275
                                                    435/325

OTHER PUBLICATIONS

Coyle, Trends in Neurosci, 1988, vol. 11, p. 390.*
Kaas, Genetic Mechanisms of Memory Disorders (Excluding Alzheimer's Disease); Ed. John H. Byrne, Learning and Memory: A comprehensive reference, 2nd Ed., Academic Press, 2017, p. 371-401).*
Reeves (Nature Genetics, 1995, vol. 11, p. 177).*
Davisson, Prog. Clin. Boil. Res., 1990, vol. 360, p. 263-280.*
Kazuki (Gene Therapy, 2011, vol. 18, p. 384-393).*
Mammalian Phenotype Browser for "Increased locomotor activity", Jackson Lab, 2022.*
L. E. Olson et al., "Down Syndrome Mouse Models Ts65Dn, Ts1Cje, and Ms1Cje/Ts65Dn Exhibit Variable Severity of Cerebellar Phenotypes," Developmental Dynamics, 2004, vol. 230, pp. 581-589.
G. N. Vacano et al., "The Use of Mouse Models for Understanding the Biology of Down Syndrome and Aging," Current Gerontology and Geriatrics Research, 2011, vol. 2012, pp. 1-20.
T. Shinohara et al., "Mice containing a human chromosome 21 model behavioral impairment and cardiac anomalies of Down's syndrome," Human Molecular Genetics, 2001, vol. 10, pp. 1163-1175.
O'Doherty et al., "An Aneuploid Mouse Strain Carrying Human Chromosome 21 with Down Syndrome Phenotypes," Science, 2005, vol. 309, pp. 2033-2037.
International Search Report dated Dec. 26, 2017, in PCT/JP2017/035236.
Birling et al., "Efficient and rapid generation of large genomic variants in rats and mice using CRISMERE," Scientific Reports, Mar. 7, 2017, 7:43331, 1-11.
Office Action dated Jul. 25, 2023 in CA 3,038,638.
Office Action dated Jun. 14, 2023 in AU 2017335058.

* cited by examiner

*Primary Examiner* — Michael C Wilson
(74) *Attorney, Agent, or Firm* — Foley & Lardner LLP

(57) ABSTRACT

In this application, the provided are: a Down syndrome rat model characterized in that a rat gene homologous to at least one gene present on a human chromosome 21 or fragment thereof is a trisomy and is transmittable to progeny; or a Down syndrome rat model characterized in that it comprises a human chromosome 21 or fragment thereof, or an exogenous rat chromosome or fragment thereof on which a rat gene homologous to the human chromosome 21 or fragment thereof is present, wherein at least one gene on the human chromosome 21 or fragment thereof or on the exogenous rat chromosome or fragment thereof is added to endogenous rat genes homologous to the at least gene so as to become a trisomy and to be transmittable to progeny: and a method for producing the Down syndrome rat model.

4 Claims, 14 Drawing Sheets
Specification includes a Sequence Listing.

Rat ES(hChr.21-loxP-EGFP)

Fig. 3

| Rat ES cell line | Host embryo lineage | Number of injected embryos | Number of embryos (%) | | Recipient No. | Number of pups (%) | | Number of live male chimeras | |
|---|---|---|---|---|---|---|---|---|---|
| | | | Number of introduced embryos | Number of pups | | Number of analyzed | Number of chimeras | Number of analyzed | GT |
| Rat ES(hChr.21)2 | Crlj:WI | 12 | 12 | 9 (75) | 1727 | 9 | 8 (89) | 2 | 0 |
| | | 14 | 14 | 3 (21) | 1728 | 3 | 3 (100) | 0 | |
| | | 12 | 12 | 4 (33) | 1729 | 4 | 4 (100) | 0 | |
| | | 13 | 13 | 5 (38) | 1730 | 5 | 4 (80) | 1 | 0 |
| Rat ES(hChr.21)2 | Crlj:WI | 13 | 13 | 6 (46) | 1749 | 6 | 3 (50) | 2 | 0 |
| | | 13 | 13 | 10 (77) | 1750 | 10 | 9 (90) | 1 | 0 |
| | | 12 | 12 | 8 (67) | 1751 | 8 | 5 (63) | 3 | 0 |
| Rat ES(hChr.21)2 | Crlj:WI | 12 | 12 | 7 (58) | 1752 | 7 | 5 (71) | 4 | 0 |
| | | 12 | 12 | 10 (83) | 1753 | 10 | 9 (90) | 5 | 1 |
| | | 12 | 12 | 3 (25) | 1754 | 3 | 3 (100) | 0 | 0 |

Fig. 4

| Individual No. | Sex | Coat color chimerism (%) | GFP | Seminiferous tubule GFP |
|---|---|---|---|---|
| #1727-1 | ♂ | 70 | + | — |
| #1727-2 | ♂ | 70 | + | — |
| | | | | |
| #1730-1 | ♂ | 70 | + | — |
| | | | | |
| #1749-1 | ♂ | 85 | + | — |
| #1749-2 | ♂ | 70 | + | — |
| | | | | |
| #1750-1 | ♂ | 80 | + | — |
| | | | | |
| #1751-1 | ♂ | 40 | + | — |
| #1751-2 | ♂ | 50 | — | — |
| #1751-3 | ♂ | 60 | + | — |
| | | | | |
| #1752-1 | ♂ | 90 | + | — |
| #1752-2 | ♂ | 90 | — | — |
| #1752-3 | ♂ | 90 | + | — |
| #1752-4 | ♂ | 50 | + | — |
| | | | | |
| #1753-1 | ♂ | 90 | + | — |
| #1753-2 | ♂ | 90 | + | + |
| #1753-3 | ♂ | 85 | + | — |
| #1753-4 | ♂ | 90 | + | — |
| #1753-5 | ♂ | 85 | + | — |

1753-2 (GT-chimera)

1753-3

RAT MODEL OF DOWN SYNDROME AND METHOD FOR PRODUCING SAME

CROSS-REFERENCE TO RELATED APPLICATIONS

This application is the U.S. National Stage of PCT/JP2017/035236, filed Sep. 28, 2017, which claims priority to JP 2016-190422, filed Sep. 28, 2016.

The instant application contains a Sequence Listing which has been submitted in ASCII format via EFS-WEB and is hereby incorporated by reference in its entirety. Said ASCII copy, created on Aug. 29, 2023, is named sequence.txt and is 6,418 bytes.

TECHNICAL FIELD

The present invention relates to a novel rat model having symptoms of Down syndrome and a method for producing the same.

BACKGROUND ART

Down syndrome (also referred to as "Down's syndrome") is a congenital disease caused by trisomy 21 in the human development process. It is known that Down syndrome gives rise to impaired phenotypes such as mental retardation, heart malformation, Early-onset Alzheimer's disease, infantile leukemia, and immune system abnormality. Moreover, since Down syndrome is caused by chromosome abnormality, there are no therapeutic methods therefor. Furthermore, the mechanism that develops various disorders of Down syndrome has been hardly clarified. Further, with regard to the phenotypes of Down syndrome-bearing patients, what genes (or a gene group) correspond to the symptoms found in Down syndrome, or the correlation between phenotypes and genotypes, have not yet been clarified.

Under such circumstances, in order to elucidate the mechanism of the development of Down syndrome, and also, in order to develop a therapeutic method for alleviating the symptoms thereof, Down syndrome mouse models had been produced. For example, Ts1Cje and Ts65Dn mice are mouse models having a rearranged chromosome 16 (Non Patent Literature 1, Non Patent Literature 2, and Non Patent Literature 3). The Ts65Dn mouse was produced by: irradiating the testis of a male mouse; mating the male mouse with a female mouse; and then selecting trisomic mice with chromosomal rearrangement. In addition, apart from the Ts65Dn mouse, a Down syndrome mouse model comprising human chromosome 21 was produced, and it was described that the Down syndrome mouse model exhibits abnormal behavior or cardiac abnormality found in Down syndrome (Non Patent Literature 4 and Non Patent Literature 5). This mouse was obtained by injecting human chromosome 21-introduced mouse embryonic stem (ES) cells into a mouse 8-cell embryo or blastocyst-stage embryo, transplanting the embryo into the uterus, and selecting desired mice from born chimeric mice and progenies thereof.

It is known that a rat is preferable as an animal model replaced for mice because the rat can be tested for sophisticated cognitive functions. However, since it is extremely difficult to produce a rat model, no Down syndrome rat models have been produced so far.

PRIOR ART LITERATURE

Non Patent Literature

Non Patent Literature 1: M. T. Davisson et al., "Segmental trisomy of murine chromosome 16: a new model system for studying Down syndrome," in Molecular Genetics of Chromosome 21 and Down Syndrome, D. Patterson and C. J. Epstein, Eds., pp. 263-280, Wiley-Liss, NY, USA, 1990

Non Patent Literature 2: L. E. Olson et al., Developmental Dynamics 2004; 230(3): 581-589

Non Patent Literature 3: G. N. Vacano et al., "The use of mouse models for understanding the biology of Down Syndrome and aging," in Current Gerontology and Geriatrics Research, Volume 2012, Article ID 717315, Hindawi Publishing Corporation Non Patent Literature 4: T. Shinohara et al., Human Molecular Genetics 2001; 10(11): 1163-1175

Non Patent Literature 5: A. O'Doherty et al., Science 2005; 309: 2033-2037

SUMMARY OF INVENTION

Problem to Be Solved By Invention

It is an object of the present invention to provide a Down syndrome rat model and a method for producing the same.

As mentioned above, it is known that, differing from mouse models, production of a Down syndrome rat model is extremely difficult. A reason therefor is that rat ES cells transmittable to progeny could not be obtained. Moreover, as with the aforementioned Non Patent Literature 5, even if a human chromosome 21 is introduced into rat ES cells, followed by injecting the ES cells into an early embryo, which is then transplanted into the uterus of a rat, it is still difficult to produce a Down syndrome rat model transmittable to progeny. Furthermore, in the case of Down syndrome mouse models produced by the method described in Non Patent Literature 4, their symptoms did not necessarily correspond to the symptoms found in human patients with Down syndrome. If such a rat model is produced, it could be tested with high possibility for higher brain functions, such as cognitive functions, which are more sophisticated than mouse. As a result, since the rat model can be used to search for phenotypic abnormalities including abnormal behavior and to identify the causative genes thereof, it is considered that the rat models are highly useful for clarification of the cause of Down syndrome, development of therapeutic agents, and the like.

Solution of Problem

Through intensive studies, the present inventors have applied a combination of producing rat ES cells (a male rat lineage), microcell mediated chromosome transfer (MMCT), round spermatid injection (ROSI), and other methods, so that the inventors have now succeeded in production of a Down syndrome rat model transmittable to progeny for the first time, thereby completing the present invention.

Thus, the present invention includes the following characteristics.

(1) A Down syndrome rat model characterized in that a rat gene homologous to at least one gene present on human chromosome 21 or a fragment thereof is a trisomy and is transmittable to progeny.

(2) A Down syndrome rat model characterized in that it comprises a human chromosome 21 or fragment thereof, or an exogenous rat chromosome or fragment thereof on which a rat gene homologous to the human chromosome 21 or fragment thereof is present, wherein at least one gene present on the human chromosome 21 or fragment thereof or on the exogenous rat chromosome or fragment thereof is added to endogenous rat genes homologous to the at least one gene so as to become a trisomy and to be transmittable to progeny.

(3) The Down syndrome rat model according to the above (2), wherein the human chromosome 21 or fragment thereof, or the exogenous rat chromosome or fragment thereof, is retained at a retention rate of 80% to 90% or more in tissues of rat progeny.

(4) The Down syndrome rat model according to the above (2) or (3), which has abnormal behavior including anxiety-like behavior or memory disorders, in comparison to healthy rats.

(5) The Down syndrome rat model according to any of the above (2) to (4), wherein the fragment of the human chromosome 21 or the fragment of the exogenous rat chromosome comprises a centromere region and has a size of 10 to 34 Mb.

(6) The Down syndrome rat model according to any of the above (2) to (5), wherein the human chromosome 21 or fragment thereof or the exogenous rat chromosome or fragment thereof comprises DNA encoding a fluorescent protein.

(7) A method for producing the Down syndrome rat model transmittable to progeny according to any of the above (2) to (6), wherein the method comprises the following steps of:

fusing microcells comprising a human chromosome 21 or fragment thereof, or an exogenous rat chromosome or fragment thereof on which a rat gene homologous to the human chromosome 21 or fragment thereof is present, with ES cells of a male rat lineage by a microcell-mediated chromosome transfer method, thereby to produce ES cells comprising the human chromosome 21 or fragment thereof or the exogenous rat chromosome or fragment thereof, at least one gene present on the human chromosome 21 or fragment thereof or the exogenous rat chromosome or fragment thereof is added to endogenous rat genes homologous to the at least one gene so as to become a trisomy;

introducing the ES cells into a rat blastocyst-stage embryo or 8-cell embryo, and then transplanting the obtained embryo into the uterus of a rat surrogate mother to produce chimeric rats;

conducting micro-insemination of the ovum of a rat with round spermatids obtained from the produced male chimeric rat according to round spermatid injection (ROSI), or micro-insemination of the ovum of a rat with the elongated spermatids of the male chimeric rat according to elongated spermatid injection (ELSI), or micro-insemination of the ovum of a rat with the sperm of the male chimeric rat according to intracytoplasmic sperm injection (ICSI), thereby to produce rat progeny; and selecting a rat transmittable to progeny, which retains the human chromosome 21 or fragment thereof or the exogenous rat chromosome or fragment thereof, from the rat progeny.

(8) The method according to the above (7), wherein the human chromosome 21 or fragment thereof or the exogenous rat chromosome or fragment thereof comprises DNA encoding a fluorescent protein.

(9) The method according to the above (7) or (8), wherein the fragment of the human chromosome 21 or the fragment of the exogenous rat chromosome comprises a centromere region and has a size of 10 to 34 Mb.

According to the present invention, a Down syndrome rat model transmittable to progeny is provided. Since a human chromosome 21 or fragment thereof or an exogenous rat chromosome or fragment thereof, which has been introduced into the Down syndrome rat model transmittable to progeny, is extremely stably retained, this rat is useful as a Down syndrome animal model, and is useful for development of a pharmaceutical product for Down syndrome, development of a therapeutic method therefor, clarification of a mechanism of the onset, and the like.

The present description includes all or part of the contents as disclosed in Japanese Patent Application No. 2016-190422, from which the present application claims priority.

BRIEF DESCRIPTION OF DRAWINGS

FIG. 3 shows a summary of the production results of chimeric rats produced from rat ES (hChr.21-loxP-EGFP). In the table, GT indicates the number of male individuals, in which germ-line transmission occurred.

FIG. 4 shows the percentages of coat color chimerism of ES cells, the presence or absence of GFP positive cells in the whole body, and the presence or absence of GFP-positive cells at the seminiferous tubule, in some of chimeric male rats (chimerism: 40% or more) produced from rat ES (hChr.21-loxP-EGFP). It is found that only one rat (#1753-2), which was GFP-positive at the seminiferous tubule, was obtained.

DESCRIPTION OF EMBODIMENTS

Figure 1:
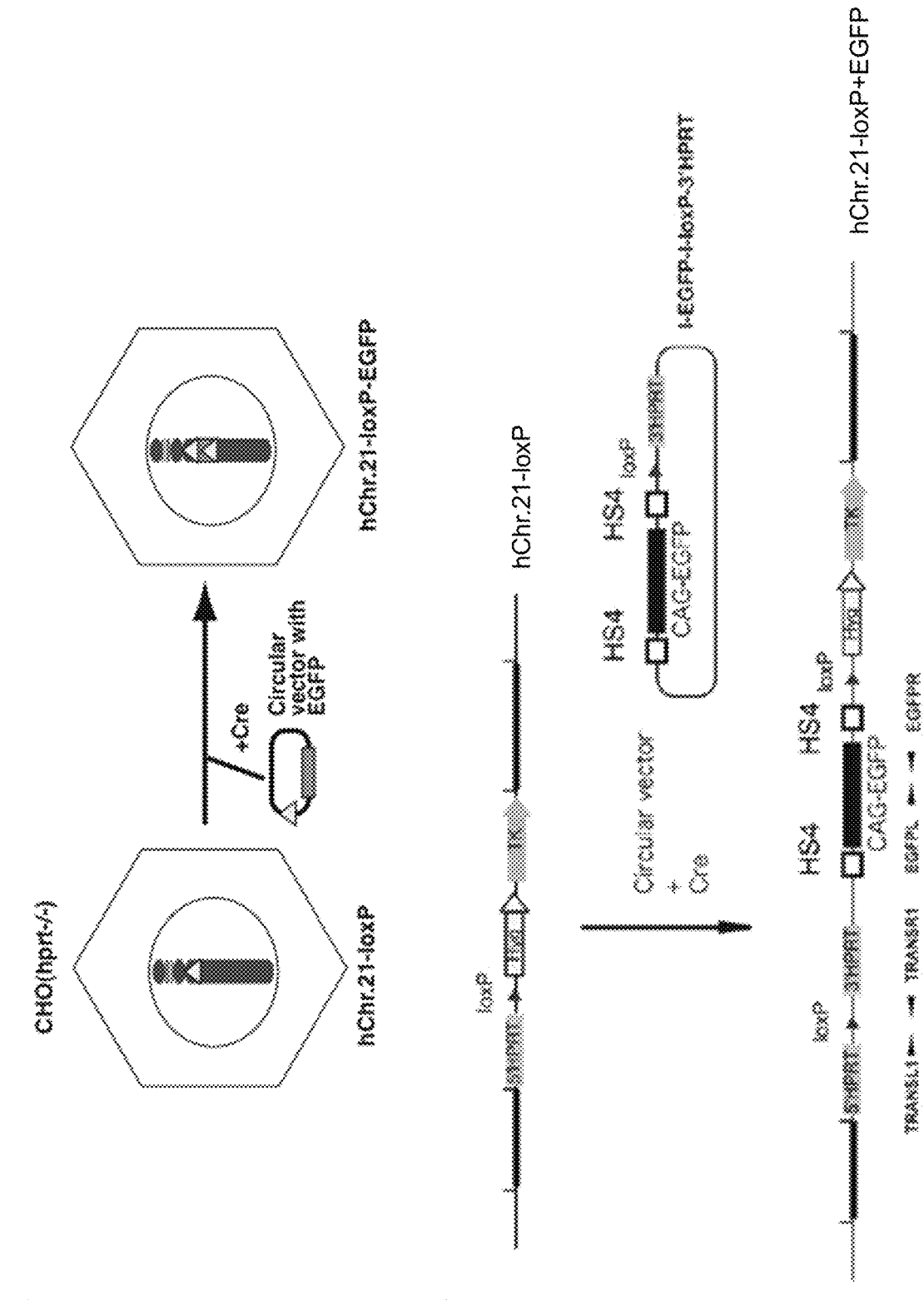
FIG. 1a is a schematic view of the procedures of Example 1.
FIG. 1b shows a partial structure of hChr.21-loxP allele before recombination, an EGFP introducing vector (I-EGFP-I-loxP-3'HPRT), and a partial structure of the allele of a modified human chromosome 21 (hChr.21-loxP-EGFP) that has been subjected to Cre-loxP recombination by the aforementioned vector. In the figure, CHO indicates Chinese hamster ovary cells, hChr.21 indicates human chromosome 21, EGFP indicates DNA encoding the fluorescent protein, HPRT or hprt indicates a hypoxanthine phosphoribosyl transferase gene, Hyg indicates a hygromycin resistant gene, and TK indicates a thymidine kinase gene.

The present invention will be described more specifically.

1. Production of Down Syndrome Rat Model

The Down syndrome rat model of the present invention can be produced by a method comprising a combination of: production of rat ES cells (male rat lineage); microcell mediated chromosome transfer (MMCT); round spermatid injection (ROSI) or intracytoplasmic sperm injection (ICSI) or elongated spermatids injection (ELSI); and selection.

Specifically, the Down syndrome rat model transmittable to progeny of the present invention can be produced as follows. The production method comprises the following steps of: fusing microcells comprising a human chromosome 21 or fragment thereof, or an exogenous rat chromosome or fragment thereof on which a rat gene homologous to the human chromosome 21 or fragment thereof is present, with ES cells of a male rat lineage by a microcell-mediated chromosome transfer method, thereby to produce ES cells comprising the human chromosome 21 or fragment thereof or the exogenous rat chromosome or fragment thereof, at least one gene on the human chromosome 21 or fragment thereof or the exogenous rat chromosome or fragment thereof is added to endogenous rat genes homologous to the at least one gene so as to become a trisomy; introducing the ES cells into a rat blastocyst-stage embryo or 8-cell embryo, and then transplanting the obtained embryo into the uterus of a rat surrogate mother to produce chimeric rats; conducting micro-insemination of the ovum of a rat with round spermatids obtained from the obtained male chimeric rat according to round spermatid injection (ROSI), or micro-insemination of the ovum of a rat with the elongated spermatids of the male chimeric rat according to elongated spermatid injection (ELSI), or micro-insemination of the ovum of a rat with the sperm of the male chimeric rat according to intracytoplasmic sperm injection (ICSI), thereby to produce rat progeny; and selecting a rat transmittable to progeny, which retains the human chromosome 21 or fragment thereof or the exogenous rat chromosome or fragment thereof, from the rat progeny.

According to one embodiment of the invention, in the above-described method, the human chromosome 21 or fragment thereof or the exogenous rat chromosome or fragment thereof may comprise a selective marker gene for selecting the chromosome, such as, for example, DNA encoding a fluorescent protein (which is referred to as a "fluorescent gene").

Alternatively, the Down syndrome rat model of the invention may be a Down syndrome rat model, which is characterized in that a rat gene homologous to at least one gene present on a human chromosome 21 or fragment thereof becomes a trisomy and is transmittable to progeny.

The term "a human chromosome 21 or fragment thereof" is used herein to mean, unless otherwise specified, any of: a substantially complete human chromosome 21; a chromosomal fragment of the complete human chromosome 21, comprising a centromere and having a size of approximately 10 Mb to approximately 34 Mb; a modified form of the substantially complete human chromosome 21 or the chromosomal fragment thereof, which comprises a foreign gene or foreign DNA in the nucleotide sequence thereof; and a modified form of the substantially complete human chromosome 21, the chromosomal fragment thereof, or the modified form thereof, in which the human centromere is substituted with a mouse centromere (e.g., the centromere of mouse chromosome 11 or mouse chromosome 16).

Herein, the "substantially complete human chromosome 21" preferably indicates an intact (namely, complete) human chromosome 21, and it means human chromosome 21, which may comprise a minor alternation on the nucleotide sequence that may occur in the process of chromosome introduction operation or may occur incidentally in the cell nucleus of a rat model (i.e., an alternation that may not affect the phenotype of Down syndrome).

Herein, with regard to the "chromosomal fragment of the complete human chromosome 21, comprising a centromere and having a size of approximately 10 Mb to approximately 34 Mb," this chromosomal fragment preferably comprises a region for retaining the function of a chromosome and a long arm region affecting the phenotype of Down syndrome. The "region for retaining the function of a chromosome" comprises a telomeric region, the entire or a part of long arm region, and the like, as well as the centromere region. In addition, with regard to the "long arm region affecting the phenotype of Down syndrome," since such phenotype varies, it is difficult to completely specify the region. However, the long arm region includes, at least, a region that has been assumed at the current stage, for example, a region that is assumed to be associated with mental retardation, etc., such as q22.1 or q22.2. The above-described chromosomal fragment is a chromosomal fragment of complete human chromosome 21, comprising a centromere and having a size of approximately 10 Mb to approximately 34 Mb, preferably approximately 20 Mb to approximately 34 Mb, and more preferably approximately 30 Mb to approximately 34 Mb. The genome of such a human chromosome 21 has been decoded (M. Hattori et al., Nature 2000; 405: 311-319), and it has been found that at least 225 genes are present in a fragment with a size of approximately 34 Mb.

Herein, with regard to the "modified form of the substantially complete human chromosome 21 or the chromosomal fragment thereof, which comprises a foreign gene or foreign DNA in the nucleotide sequence thereof," as described above, the foreign gene or the foreign DNA is preferably a selective marker gene for selecting cells comprising the above-described chromosome or a chromosomal fragment thereof, for example, DNA encoding a fluorescent protein ("fluorescent gene").

The phrase "exogenous rat chromosome or fragment thereof, on which a rat gene homologous to the human chromosome 21 or a fragment thereof is present" is used herein to mean a rat chromosome or fragment thereof comprising a rat gene homologous to a gene on the human chromosome 21 or fragment thereof, which is exogenously introduced into the cell nucleus, and more preferably means a rat chromosome or fragment thereof comprising a rat gene homologous to a gene on a Down Syndrome Critical Region (DSCR), which is exogenously introduced into the cell nucleus. As in the case of the above-described human chromosome 21 or fragment thereof, this rat chromosome or fragment thereof is used to mean, unless otherwise specified, any of: a substantially complete rat chromosome; a chromosomal fragment of the complete rat chromosome, comprising a centromere and having a size of at least approximately 10 Mb; a modified form of the substantially complete rat chromosome or the chromosomal fragment thereof, which comprises a foreign gene or foreign DNA in the nucleotide sequence thereof; and a modified form of the substantially complete rat chromosome, the chromosomal fragment thereof, or the modified form thereof, in which the rat centromere is substituted with a mouse centromere (e.g., the centromere of mouse chromosome 11 or mouse chromosome 16).

The Down syndrome rat model of the invention, which is characterized in that a rat gene homologous to at least one gene present on human chromosome 21 or fragment thereof is a trisomy and is transmittable to progeny, includes not only the above-described Down syndrome rat model comprising a human chromosome 21 or a fragment thereof, or an exogenous rat chromosome or fragment thereof on which a rat gene homologous to the human chromosome 21 or fragment thereof is present, but also includes a Down syndrome rat model, in which the above-described at least one, preferably a plurality of rat genes are doubly comprised on the endogenous rat chromosome, so that the rat model becomes genetically trisomic. The technique of duplicating a gene on the chromosome include the technique described, for example, in L. E. Olson et al., Science 2004, 306: 687-690.

Hereafter, the present method will be further specifically described.

(1) Production of Rat ES Cells (Male Lineage)

As in the mouse ES cell (M. J. Evans and M. H. Kaufman, Nature 1981; 292(5819): 154-156), the rat ES cell is a cell line having pluripotency and self-replication ability, which is established from the inner cell mass of a rat blastocyst-stage embryo or 8-cell embryo. For instance, the rat blastocyst, which is obtained by dissolution of egg zona pellucida of a rat embryo, is cultured on a mouse embryonic fibroblast (MEF) feeder, using a medium supplemented with a leukemia inhibitory factor (LIF). Then, 7 to 10 days after the culture, an outgrowth formed from the blastocyst is dispersed and then transferred onto a MEF feeder, followed by culturing it. Approximately 7 days later, ES cells appear. The production of rat ES cells is described, for example, in K. Kawaharada et al., World J Stem Cells 2015; 7(7): 1054-1063.

ES cells include a female lineage and a male lineage. In the present invention, male lineage rat ES cells, and more preferably, male lineage rat ES cells produced from hybrid rats may be used. By using such ES cells together with the ROSI method and a fluorescence selection method, a rat model transmittable to progeny can be obtained. The male lineage ES cells can be selected by analyzing the XY karyotype of the produced ES cell lines, using XY chromosome probes (for example, available from Chromosome Science Labo Inc., etc.). The term "male lineage ES cell(s)" or "ES cell(s) (male lineage-)" used herein refers to ES cell(s) having XY karyotype.

In the aforementioned Non Patent Literatures 4 and 5, when a Down syndrome mouse model was produced, female lineage ES cells were used, but when male lineage ES cells were used, they failed to establish mice transmittable to progeny (Non Patent Literature 5). Considering this point, it would be found that various trials and errors have been repeatedly carried out to produce the Down syndrome rat model of the present invention. That is to say, in fact, such a rat model had not been established.

Induced pluripotent stem (iPS) cells have been known as stem cells similar to ES cells (K. Takahashi and S. Yamanaka, Cell 2006; 126(4): 663-676; K. Takahashi et al., Cell 2007; 131(5): 861-872). Rat iPS cells have also been produced by a method similar to the above (W. Li et al., Cell Stem Cell 2009; 4: 16-19; S. Hamanaka et al., PLoS One 2011; 6: e22008). That is, according to W. Li et al. (ibid.), WB-F344 rat liver endothelial cells are transduced with Oct4, Sox2 and Klf4 via retrovirus, and the cells are then cultured on MEF feeder cells in a common medium for mouse ES cells, which is supplemented with LIF, thereby producing rat iPS cells. Therefore, in the present invention, it is also possible to use rat iPS cells, instead of ES cells.

(2) Microcell-Mediated Chromosome Transfer (MMCT)

The microcell-mediated chromosome transfer method is also called "Microcell-Mediated Chromosome Transfer (MMCT)."

Microcells are cells comprising a small amount of cytoplasm and a micronucleus containing one or a few chromosomes, which are produced by enucleation of micronucleated cells that have been obtained by micronucleation of cells (donor cells). When these microcells are fused with recipient cells, a megabase (Mb)-size nucleic acid such as a single chromosome or a chromosomal fragment can be introduced into the cells. This fusion method is generally referred to as a "macrocell fusion method" or "microcell-mediated chromosome transfer method" (e.g., JP Patent Publication (Kokai) No. 2011-177145 A).

Donor cells capable of inducing microcells are animal cells, and more preferably mammalian cells. The types of the cells are not particularly limited, as long as the cells are able to induce microcells. The animal cells include cells with any form, such as primary cells, established cells, sub-cultured cells, cultured cells, somatic cells, and stem cells. In addition, examples of the animal cells include: invertebrate-derived cells, such as insect cells; and vertebrate-derived cells, such as mammal-derived cells such as human cells or rodent cells, bird-derived cells, amphibian-derived cells, reptile-derived cells, or fish-derived cells. The animal cells preferably include rodent cells (CHO cells, mouse A9 cells, etc.).

In order to select a microcell hybrid clone, which is obtained by fusing microcells with recipient cells, a vector having a selective marker gene (e.g., a fluorescent gene) and a loxP sequence and a Cre expression vector can be previously co-introduced into donor cells having a modified form of the human chromosome 21 (e.g., having a loxP sequence for insertion of a selective marker gene (e.g., a fluorescent gene) into a region of the human chromosome 21, such as a centromere region). According to this Cre-loxP method, a selective marker gene (e.g., a fluorescent gene) is inserted into the human chromosome 21. The human chromosome 21 having a selective marker gene (e.g., a fluorescent gene) is useful for confirming the occurrence of germ-line transmission by utilizing selective properties (e.g., fluorescence properties). Herein, the fluorescent gene is DNA encoding a fluorescent protein, and examples of the fluorescent protein include GFP, EGFP, YFP, EYFP, Venus, CFP, ECFP, Keima, and DsRed, but are not limited thereto. The amino acid sequence of such a fluorescent protein and the nucleotide sequence of DNA encoding the fluorescent protein are available from gene banks such as GenBank or known publications. For example, the amino acid sequence and nucleotide sequence of EGFP are shown in GenBank registration number LC008492 (S. Nakade et al., Nat Commun 5, 5560 (2014)). Moreover, the sequences of GFP and YFP are described, for example, in WO2012/063897A1. Even in the case of an exogenous rat chromosome, operations substantially similar to those in the case of the human chromosome 21 can be carried out.

As described above, the microcell-mediated chromosome transfer method is a technique capable of transferring an enormous nucleic acid with a size of 1 Mb or more, such as a single chromosome, a few chromosomes, or a fragment thereof, from donor cells into recipient cells. This method comprises a first step of subjecting donor cells to micronucleation, a second step of subjecting the micronucleated cells to enucleation, a third step of isolating microcells, a fourth step of fusing microcells with recipient cells, and a fifth step of selecting surviving microcell hybrid clones.

Micronucleation of donor cells can be carried out by culturing animal cells in a medium supplemented with a micronucleated cell inducer, such as colcemid, for a long period of time. Herein, the micronucleated cell inducer has an ability to induce decondensation of a chromosome and reformation of a nuclear membrane. The concentration of a micronucleated cell inducer is not limited, as long as micronucleation takes place. For example, for colcemid, its concentration is approximately 0.01 µg/ml to approximately 1 µg/ml, preferably 0.05 to 0.5 µg/ml, per $5\times10^6$ of recipient cells. By means of such micronucleation, microcells, which are cells comprising a small amount of cytoplasm and a micronucleus containing one or a few chromosomes, are formed from donor cells. For culture, conditions for the culture of donor cells are applied, and as a medium, a medium for animal cells is generally used. Examples of such a medium for animal cells include Eagle's medium (MEM), Eagle's minimal essential medium (EMEM), Dulbecco's modified Eagle's medium (DMEM), and Ham's F12 medium. The medium may be supplemented with fetal bovine serum (FBS), serum replacement (Stem Sure® Serum Replacement, etc.), and the like. The temperature is from room temperature to approximately 37° C., and the culture time is properly from approximately 40 to 80 hours.

Enucleation of micronucleated cells is carried out using cytochalasin B. A culture solution comprising the micronucleated cells is placed in a centrifugal tube, and cytochalasin B is then added in a concentration of 10 µg/ml into the tube, followed by performing centrifugation at 34° C. at approximately 11,900×g. The precipitated microcells are collected by suspending them in a serum-free medium. The microcells can be purified by ultrafiltration. The three types of membranes having pore diameters of 8 µm, 5 µm and 3 µm are prepared, and the cells are successively filtrated through these membranes.

For fusion of microcells with recipient cells, the purified microcells are multilayered on recipient cells, the culture of which has been terminated before complete confluence, and the resulting multilayered cells are then cultured. The microcell-fused cells can be selected by, for example, selection of drug resistance cell lines.

The above-mentioned fusion can be carried out by using a polyethylene glycol (PEG) method, a murine leukemia virus (MLV) method, a retro method (T. Suzuki et al., PLOS ONE, DOI: 10. 1371/journal.pone.0157187 (2016)), an MV method (M. Katoh et al., BMC Biotechnology 2010, 10: 37), and the like. The retro method comprises fusing microcells with recipient cells using ecotropic or amphotropic MLV-derived R-peptide-deleted Env (EnvAR), and this is the most efficient method applied for rodent cells. In addition, the MV method comprises promoting microcell fusion using a hemagglutinin protein (MV-H) that is measles virus fusogen and a fusion protein (MV-F). Microcells produced from donor cells, which have previously been transformed with an MV-H plasmid and an MV-F plasmid, easily cause cell-cell fusion with recipient cells due to the presence of fusogen expressed on the surface of the cell membrane.

Preferably, a foreign nucleic acid, such as a human chromosome, has previously been introduced into donor cells. In this case, the human chromosome transfers into microcells and then introduced into recipient cells by microcell fusion. As a result, the recipient cells are transformed with the human chromosome.

In general, microcell fusion can be preferably used to transfer (or introduce) a nucleic acid with a size of 1 Mb or more, particularly a certain megabase (Mb)-size chromosome or chromosomal fragment thereof, from a cell into another cell. In the present invention, as described above, a chromosomal fragment is a fragment of human chromosome 21, or an exogenous fragment of rat chromosome in which (one or more) genes homologous to the fragment of human chromosome 21 are present, and their chromosomal fragments preferably comprise a centromere region and have a size of approximately 10 Mb to approximately 34 Mb.

(3) Micro-Insemination Methods Including Round Spermatid Injection (ROSI)

Rat ES cells were introduced into a blastocyst-stage embryo which was then transplanted into the uterus of a surrogate mother to produce chimeric rats. Thereafter, the chimeric rats were mated to obtain offsprings. As a result, fluorescent gene expression-positive rats, i.e. transmitted rats, could not be obtained. Thus, the ability transmittable to progeny according to the ROSI method was examined. As a result, rats stably retaining a desired human chromosome 21 or fragment thereof or a desired exogenous rat chromosome or fragment thereof, which were transmittable to progeny, could be obtained with extremely low probability.

The ROSI (Round Spermatid Injection) method comprises chopping the seminiferous tubule removed from the testis of the above-described chimeric rat (male), preparing a suspension thereof, suctioning round spermatids from the suspension into a pipette to allow the nuclei and cytoplasm to disperse in the pipette, and then injecting the resultant dispersion into the ovum of a rat for micro-insemination (C. Tsurumaki et al., J. Mamm. Ova Res. 2009; 26: 86-93 (Jp)). Alternatively, it is also possible to obtain round spermatids from rats by ejaculation. The fertilized ovum is transplanted into the uterus of a surrogate mother, and subsequently chimeric rats are obtained from the surrogate mother. Thereafter, female rats (or male rats) retaining a human chromosome 21 or fragment thereof or an exogenous rat chromosome or fragment thereof are mated with pure-line or hybrid, preferably hybrid male rats (or female rats), so that karyotype-stable trisomic rats can be obtained, in which the human chromosome is retained in approximately 80% to 90% or more of the cell nuclei in various types of tissues of the rats.

It is also possible to conduct micro-insemination of the ovum of a rat with the sperm of the above-described chimeric rat according to the known intracytoplasmic sperm injection method (ICSI), instead of the ROSI method. Alternatively, it is also possible to conduct micro-insemination of the elongated spermatids of the above-described chimeric rat with the ovum of a rat according to the known elongated spermatid injection (ELSI).

(4) Selection

The method of selecting Down syndrome rat models transmittable to progeny from the rats produced by mating in the above (3) comprises: measuring positive expression rates of a fluorescence gene in blood cells, peripheral blood, bone marrow or spleen by using flow cytometry (FCM); performing a comprehensive analysis by employing PCR, a CGH array, a next-generation sequencer, or the like using tail DNA or the like, thereby analyzing a region retaining a human chromosome 21 or fragment thereof; analyzing different types of tissues (e.g., brain, thymus gland, heart, lung, liver, spleen, kidney, small intestine, testis, etc.) according to the FISH (Fluorescence In Situ Hybridization) method, so that the retention of a human chromosome 21 or fragment thereof or an exogenous rat chromosome or fragment thereof, or a retention rate, is measured; measuring abnormal behavior, cognitive function disorders and the like by a light/dark test, an open field test, an elevated plus maze test, etc.; measuring abnormity in the brain or heart by using MRI, CT, etc.; confirming gene expression on the human chromosome 21 or fragment thereof by an RT-PCR method, a microarray method, or a next-generation sequencing method; etc. In the FISH method, a fluorescence-labeled specific oligonucleotide probe is used to hybridize with a gene on the human chromosome 21 or fragment thereof, and the chromosome is then detected using a fluorescence microscope. A rat selected by these methods can be determined to be a Down syndrome rat model, which is characterized in that it stably has a human chromosome 21 or a fragment thereof having the phenotypes of Down syndrome, and is transmittable to progeny.

The phrase "transmittable to progeny" is used herein to refer to that the above-defined human chromosome 21 or fragment thereof or the above-defined exogenous rat chromosome or fragment thereof is stably transmitted to progeny (or offsprings) according to germ-line transmission.

(5) Specific Production Procedures

Specific production procedures may comprise, for example, the following steps.

(Step 1)

An EGFP gene is introduced onto the above-defined human chromosome 21 or fragment thereof or the above-defined exogenous rat chromosome or fragment thereof, retaining loxP in a centromere region thereof, in rodent cells such as CHO cells, by using the Cre-loxP system, and subsequently, whether the human chromosome 21 region or fragment thereof or the exogenous rat chromosome or fragment thereof is retained is confirmed by PCR and FISH methods.

(Step 2)

The above-described modified human chromosome 21 or fragment thereof or the above-described e xogenous rat chromosome or fragment thereof is introduced into rat ES cells (male lineage) according to the microcell-mediated chromosome transfer method, and thereafter, whether a region of the human chromosome 21 or fragment thereof or a region of the exogenous rat chromosome or fragment thereof is retained is confirmed by PCR and FISH methods.

(Step 3)

The above-described rat ES cells are injected into a blastocyst-stage embryo, and the embryo is then transplanted into the uterus of a surrogate mother, thereby to produce chimeric rats.

(Step 4)

Using the round spermatids, sperm or elongated spermatids from the above-described chimeric male rat and the ovum from a female rat, micro-insemination is carried out according to the round spermatid injection method, the intracytoplasmic sperm injection method, or the elongated spermatid injection method, thereby to produce rats transmittable to progeny. Subsequently, using the DNA and cells of the rat tails, whether the human chromosome 21 or fragment thereof or the exogenous rat chromosome or fragment thereof is retained is confirmed by PCR and FISH methods.

(Step 5)

According to mating, trisomic rats are bred.

(Step 6)

The GFP-positive rate in blood cells is measured by FCM analysis.

(Step 7)

According to the flow cytometry (FCM) analysis, in which various types of blood cell lineage-specific antibodies are used, the fluorescent gene expression-positive rate in the blood cell lineage is measured.

(Step 8)

Various types of tissues are collected, and the rate of retaining the human chromosome 21 or fragment thereof or the exogenous rat chromosome or fragment thereof is measured in the tissues by FISH analysis.

(Step 9)

The expression of genes on the human chromosome 21 or fragment thereof or the exogenous rat chromosome or fragment thereof in various types of tissues is confirmed by RT-PCR method.

(Step 10)

The obtained rats are compared with healthy rats according to various types of behavior analyses, analyses of abnormality in the brain or heart, or the like.

2. Characteristics of Down Syndrome Rat Model

The Down syndrome rat model of the present invention has the following characteristics.

In general, in comparison to a Down syndrome mouse model, when an electrophysiological experiment is performed on a Down syndrome rat model, or when a substance, such as a drug, is injected into a specific site such as t nucleus of the brainstem, the size of the brain of a rat is appropriate, and, while in mice, because the spontaneous activities are high, tests like cognitive function tests give ambiguous results in many cases, in rats sophisticated cognitive function tests for higher brain dysfunction can be carried out because of having low spontaneous activities and high intelligence. Thus, advantages of using rats are known.

The Down syndrome rat model of the present invention had not previously been produced. A reason is that there were considerable difficulties in production of Down syndrome rat models, as described above. The currently produced Down syndrome rat is characterized: in that it stably retains, in the nucleus, an exogenously introduced human chromosome 21 or fragment thereof or an exogenously introduced rat chromosome or fragment thereof (preferably one of them); in that at least one gene or preferably a plurality of genes present on the introduced human chromosome 21 or fragment thereof or exogenous rat chromosome or fragment thereof are added to endogenous rat genes that are homologous to the aforementioned gene or genes, so as to become a trisomy; in that the rat has phenotypes of Down syndrome; in that the rat is transmittable to progeny; and the like. Herein, the term "homologous" refers to that nucleotide sequences of mature genes share a sequence identity of approximately 70% or more, or that the biological functions of two genes are substantially equivalent to each other. The sequence identity indicates a percentage (%) of the number of matched nucleotides relative to the total number of nucleotides comprising gaps, which percentage is obtained when the mature sequence of a human gene is aligned to the mature sequence of a rat gene are aligned to result in the highest matching percentage, and is then compared to each other. In addition, with regard to the above-described trisomy, because it is known that a region homologous to human chromosome 21 gene is present on rat chromosomes 11 and 20, endogenous rat genes (2 copies) and an exogenous human gene (1 copy) or an exogenous rat gene (1 copy) genetically become a trisomy. For example, a rat model comprising a human chromosome 21 fragment containing such a genetically homologous region becomes genetically trisomic.

Individual characteristics will be further described below.

(1) The Down Syndrome Rat Model of the Present Invention Stably Retains, in the Cell Nucleus Thereof, a Human Chromosome 21 or Fragment Thereof or an Exogenous Rat Chromosome or Fragment Thereof.

The presence of the above-defined genes on human chromosome 21 or fragment thereof or on exogenous rat chromosome or fragment thereof (e.g., the genes described in Non Patent Literatures 4 and 5) can be confirmed by PCR analysis. Moreover, the presence of the human chromosome 21 or fragment thereof or the exogenous rat chromosome or fragment thereof in blood cells or various types of tissues of a rat, or the retention rate thereof, can be confirmed by FISH analysis or flow cytometric analysis.

In any of peripheral blood, bone marrow, and spleen, the rate of retaining a human chromosome 21 or fragment thereof or an exogenous rat chromosome in immune cells, such as $CD61^+/CD45RA^-$ (NK cell-like), $CD3^+/CD4^+$ ($CD4^+$ T cells), $CD3^+/CD8^+$ ($CD8^+$ T cells), and $CD45R^+$ (B cell-like) cells, is 90% or more, preferably 95% or more, and further preferably 98% or more.

Moreover, the rate of retaining a human chromosome 21 or fragment thereof or an exogenous rat chromosome or fragment thereof in various types of tissues (e.g., brain, thymus gland, heart, lung, liver, spleen, kidney, small intestine, testis, bone marrow, etc.) is 80% to 90% or more, preferably 95% or more, and further preferably 98% or more.

As described above, the Down syndrome rat model stably retains, in the cell nucleus thereof, a human chromosome 21 or fragment thereof or an exogenous rat chromosome or fragment thereof, so that a completely or substantially complete human chromosome 21 or an exogenous rat chromosome, or endogenous rat genes homologous to at least one gene present on a human chromosome 21 or fragment thereof or an exogenous rat chromosome or fragment thereof, forms a trisomy.

(2) The Down Syndrome Rat Model of the Present Invention has the Phenotypes of Down Syndrome.

The Down syndrome rat model is confirmed to have phenotypes such as anxiety-like behavior or memory disorders according to behavior analysis.

(3) The Down Syndrome Rat Model of the Present Invention is Transmittable to Progeny.

A human chromosome 21 or fragment thereof or an exogenous rat chromosome or fragment thereof is transmitted to progeny (offsprings) according to germ-line transmission. In the Down syndrome rat model, the human chromosome 21 or fragment thereof or the exogenous rat chromosome or a fragment thereof is extremely stably retained.

EXAMPLES

Hereinafter, the present invention will be more specifically described referring to the following examples. However, these examples are not intended to limit the technical scope of the present invention. In the examples, a Down syndrome rat model comprising a human chromosome 21 or fragment thereof will be specifically described. The above-described Down syndrome rat model comprising an exogenous rat chromosome or fragment thereof can also be produced by the same method as that for the Down syndrome rat model comprising a human chromosome 21 or fragment thereof.

Example 1

Production of Human Chromosome 21
hChr.21-loxP-EGFP Comprising EGFP

[A] Transfer of hChr.21-loxP into CHO Cells
[A.1] Microcell Mediated Chromosome Transfer and Isolation of Drug Resistance Clones As recipient cells, DT40 (hChr.21-loxP), which retained a modified human chromosome 21 and had a loxP sequence introduced around the long arm centromere of human chromosome 21, was used, as described by Kazuki et al. (Gene Therapy, 18: 384-393, 2011). DT40 (hChr.21-loxP) was cultured in cell culture dishes, and at the time point when the cells became confluent, the medium was exchanged with an RPMI1640 medium supplemented with 20% FBS, 1% chicken serum, 10-4 M 2-mercaptoethanol, and 0.05 μg/ml colcemid, and subsequently, the cells were further cultured for 12 hours to form microcells. The culture medium was replaced with 24 ml of a serum-free DMEM medium, and the culture was then dispensed in an amount of 2 ml each into 12 flasks for centrifugation (25 cm$^2$, Corning) d previously coated with 100 μ/ml poly-L-lysine, followed by performing culture at 37° C. for 30 minutes, thereby adhering the cells onto the bottom of each flask. A supernatant was removed, and the centrifugal flask was then filled with a cytochalasin B (10 mg/ml, Sigma) solution previously warmed at 37° C. to perform centrifugation at 34° C. at 8000 rpm for 1 hour. Thereafter, the microcells were suspended in a serum-free DMEM medium, and the suspension was then purified through filters having sizes of 8 μm, 5 μm and 3 μm. After purification, the microcells were centrifuged at 1700 rpm for 10 minutes and then suspended in 5 ml of a serum-free DMEM medium.

As a donor cell, CHO (HPRT), namely CHO hprt-deficient cell (which was obtained from Health Science Research Resources Bank (Osaka, Japan), Registration No. JCRB0218) was used. The purified micronucleated cells were suspended again in 2 ml of a serum-free culture solution containing PHA-P (SIGMA), and the suspension was then gently seeded on CHO cells, from which the culture supernatant [10% FBS-added F12 medium (Invitrogen)] was removed. The plate was incubated at 37° C. for 15 minutes. The supernatant was removed, and then, the fusion was conducted using 1 ml of a PEG1000 (Wako) solution [wherein 5 g of PEG1000 was completely dissolved in a serum-free DMEM medium, and 1 ml of dimethyl sulfoxide (DMSO) was then added thereto, followed by sterilization with filters] precisely for 1 minute. The resultant cells were washed with 4 ml of a serum-free culture solution (DMEM) four times, and 5 ml of a normal culture solution of CHO cells was then added, followed by overnight incubation. The cell surface was washed with PBS(−) twice, and the cells were then treated with trypsin so that the cells were dispersed. The cell dispersion was seeded on five cell culture dishes having a diameter of 10 cm, and G418 was then added thereto to a concentration of 800 μg/ml, followed by performing selection culture for 1 to 2 weeks. The microcell mediated chromosome transfer was carried out twice, so that a total of six resistant colonies were isolated and were allowed to grow, and the subsequent analysis was then carried out (clone name: CHO (HPRT; hChr.21-loxP)).

[A.2] Selection of Drug Resistance Clones

[A.2.1] PCR Analysis

In order to extract the genomic DNA of G418-resistant cell line and then to select recombinant clones using the genomic DNA as templates, PCR was carried out using the following primers, and whether hChr.21-loxP was introduced into CHO cells was confirmed. The sequences of the primers are as follows.

```
#21CEN<1>2L:
                                       (SEQ ID NO: 1)
5'-aaatgcatcaccattctcccagttaccc-3'

PGKr1:
                                       (SEQ ID NO: 2)
5'-ggagatgaggaagaggagaaca-3'

D21S265-L:
                                       (SEQ ID NO: 3)
5'-gggtaagaaggtgcttaatgctc-3'

D21S265-R:
                                       (SEQ ID NO: 4)
5'-tgaatatgggttctggatgtagtg-3'

D21S261-L:
                                       (SEQ ID NO: 5)
5'-gaggggactgggacaagccctttgctggaagaga-3'

D21S261-R:
                                       (SEQ ID NO: 6)
5'-acattaggaaaaatcaaaaggtccaattattaagg-3'

D21S268-L:
                                       (SEQ ID NO: 7)
5'-caacagagtgagacaggctc-3'

D21S268-R:
                                       (SEQ ID NO: 8)
5'-ttccaggaaccactacactg-3'

D21S266-L:
                                       (SEQ ID NO: 9)
5'-ggcttggggacattgagtcatcacaatgtagatgt-3'

D21S266-R:
                                       (SEQ ID NO: 10)
5'-gaagaaaggcaaatgaagacctgaacatgtaagtt-3'

D21S1259-L:
                                       (SEQ ID NO: 11)
5'-gggactgtaataaatattctgttgg-3'

D21S1259-R:
                                       (SEQ ID NO: 12)
5'-cactggctctcctgacc-3'

CBR-L:
                                       (SEQ ID NO: 13)
5'-gatcctcctgaatgcctg-3'

CBR-R:
                                       (SEQ ID NO: 14)
5'-gtaaatgccctttggacc-3'
```

Using GeneAmp9600 manufactured by Perkin-Elmer as a thermal cycler, and also using Ex Taq (Takara Bio, Inc., Kyoto, Japan) as Taq polymerase, PCR was carried out with the use of a buffer and dNTPs (dATP, dCTP, dGTP, and dTTP) under recommended conditions as mentioned in the attached instruction. With regard to the temperature and cycle conditions, after thermal degeneration at 93° C. for 5 minutes, the reaction was performed for 35 cycles where one cycle consisted of 93° C.-1 minute, 56° C.-1 minute, and 72° C.-1 minute. As a result of the PCR, all 6 clones obtained were positive for all the primer sets. As such, the 6 clones were used in analyses as described below.

[A.2.2] Mono-Color FISH Analysis

Among the above-obtained CHO (HPRT; hChr.21-loxP), 6 clones were subjected to FISH analysis using human cotI DNA as a probe according to the method described by Matsubara et al. (FISH Experimental Protocols, Shujunsha (Tokyo, Japan), 1994). As a result, it was confirmed that, in 3 out of the 6 clones, CHO (HPRT; hChr.21-loxP) was introduced into the CHO cells at a rate of 80% or more.

From the above-described results, it was concluded that hChr.21-loxP could be introduced into the CHO cells.

[B] Insertion of EGFP Gene into hChr.21-loxP in hChr.21-loxP-Containing CHO Cells According to Cre/loxP System

[B.1] Transfection and Isolation of HAT Resistance Clones

Gene introduction was carried out for the above-obtained CHO (HPRT; hChr.21-loxP)-3 by using a lipofection method. Thereafter, 1 mg of Cre and 2 mg of the EGFP insertion vector (I-EGFP-I-loxP-3'HPRT) described by Kazuki et al. (Gene Therapy, 18: 384-393, 2011) were introduced into the gene-introduced cells that were cultured until becoming 90% confluent in 6 wells, in accordance with commercially available protocols (Invitrogen). When the obtained cells were cultured under the condition of HAT selective culture for 2 weeks, resistant colonies appeared. A total of 6 colonies obtained by a single introduction were isolated and then allowed to grow, and the resulting colonies were then used in the following analyses (clone name: CHO (hChr.21-loxP-EGFP)).

[B.2] Selection of Drug Resistance Clones

[B.2.1] Confirming GFP-Inserted Clones By Fluorescence-Microscopic Observation

The 6 cloned colonies were observed under fluorescence microscope. As a result, GFP-positive cells were observed in all the clones, and the positive rate was almost 100%.

[B.2.2] PCR Analysis

In order to select recombinant clones using the genomic DNA of an HAT resistance cell lin as a template, PCR was carried out using the following primers, and whether a GFP gene was site-specifically inserted was confirmed. The sequences of the primers are shown below.

TRANS L1:
(SEQ ID NO: 15)
5'-tggaggccataaacaagaagac-3'

TRANS R1:
(SEQ ID NO: 16)
5'-ccccttgacccagaaattccA-3'

Using GeneAmp9600 manufactured by Perkin-Elmer as a thermal cycler, and also using LA Taq (Takara Bio, Inc.) as Taq polymerase, PCR was carried out using 2×GCI buffer and dNTPs (dATP, dCTP, dGTP, and dTTP) under recommended conditions as mentioned in the attached instruction. With regard to the temperature and cycle conditions, after thermal degeneration at 98° C. for 1 minute, the reaction was performed for 30 cycles where one cycle consisted of 94° C.-10 seconds, 60° C.-30 seconds, and 72° C.-3 minutes. As a result of the PCR, all 6 clones were found to be positive, and these 6 clones were used in the analyses described below.

[B.2.3] Mono-Color FISH Analysis

Among the above-obtained CHO (hChr.21-loxP-EGFP)), 6 clones were subjected to FISH analysis using human cotI DNA as a probe according to the method described in Matsubara et al. (FISH Experimental Protocols, Shujunsha, 1994). As a result, it was confirmed that, in 6 out of the 6 clones, one copy of hChr.21-loxP-EGFP was introduced into the CHO cells at a rate of 80% or more.

From the above-described results, it was concluded that hChr.21-loxP-EGFP could be introduced into the CHO cells.

Example 2

Production of hChr.21-loxP-EGFP-Introduced Rat ES Cells

In order to produce chimeric rats retaining hChr.21-loxP-EGFP, the hChr.21-loxP-EGFP was introduced from the CHO cells retaining hChr.21-loxP-EGFP obtained in Example 1 into rat ES cells according to the microcell-mediated chromosome transfer method.

According to the method of Tomizuka et al. (Nature Genet.16: 133-143, 1997), microcells were purified from approximately $10^8$ CHO cells retaining hChr.21-loxP-EGFP (i.e., CHO (hChr.21-loxP-EGFP)1), and were then suspended in 5 ml of DMEM. Approximately $10^7$ rat ES cells were detached by trypsin treatment, and were then washed with DMEM three times. The resulting cells were suspended in 5 ml of DMEM, and the suspension was then added to the centrifuged microcells. The obtained mixture was centrifuged at 1250 rpm for 10 minutes, and a supernatant was then completely removed. The precipitate was fully loosen by tapping, and 0.5 ml of a PEG solution [where 5 g of PEG1000 (Wako Pure Chemical Industries, Ltd. (Osaka, Japan)) and 1 ml of DMSO (Sigma) were dissolved in 6 ml of DMEM] was added at a ratio of 1:1.4 to the precipitate. The obtained mixture was fully stirred for approximately 1.5 minutes. Thereafter, 10 ml of DMEM was slowly added to the reaction mixture, and the thus obtained mixture was then centrifuged at 1250 rpm for 10 minutes. The resultant was suspended in 30 ml of an ES medium, and the suspension was then dispensed in three petri dishes (Corning) with a diameter of 100 mm, on which feeder cells were previously seeded, followed by performing culture. Twenty-four hours later, the medium was exchanged with a medium supplemented with 200 µg/ml G418, and a selective culture was then carried out for 1 week. As a result, a total of two colonies were isolated and were then allowed to grow, and were subsequently used in the analysis described below.

Figure 2:
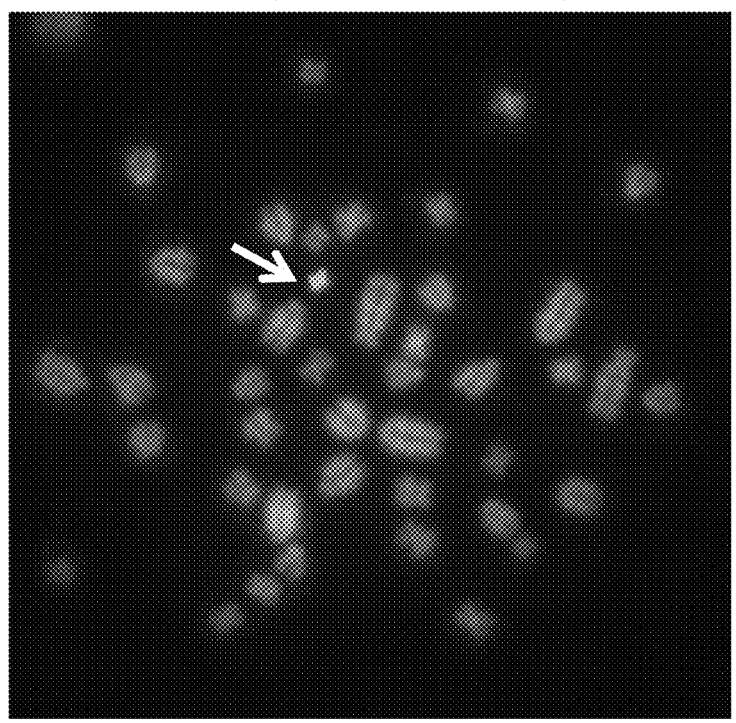
FIG. 2 shows the results of the mono-color FISH analysis of rat ES (hChr.21-loxP-EGFP) clones when human Cot-1 DNA was used as a probe. The arrow indicates the presence of hChr.21-loxP-EGFP.

Both of the two clones were found to be positive by the PCR performed using the aforementioned primers for detection of a hChr.21-loxP-EGFP region. Moreover, the above-described 2 clones were subjected to FISH analysis (Tomizuka et al., Nature Genet.16: 133-143, 1997) using human Cot-1 DNA. As a result, there was one clone, which was specifically detected using the above-described probe and whose rat karyotype was normal (FIG. 2). From the above results, it was concluded that one clone of hChr.21-loxP-EGFP-retaining rat ES cells was obtained.

From the above-described results, it was concluded that rat ES cells, into which a human chromosome 21 had been introduced, could be constructed.

Example 3

Production of hChr.21-loxP-EGFP-Introduced Rats

[A] Production of Chimeric Rats Retaining hChr.21-loxP-EGFP

Using the hChr.21-loxP-EGFP-retaining rat ES cell clone obtained in the above-described Example 2, chimeric rats were produced according to the method of Hirabayashi et al. (Mol Reprod Dev. 2010 February; 77(2): 94.doi: 10.1002/mrd.21123.). As a host, a blastocyst-stage embryo that was obtained by male-female mating of Crlj:WI rats (White, purchased from Charles River Laboratories, Japan (Yokohama, Kanagawa, Japan)) was used. Baby rats generated as a result of transplantation of the injection embryo into a rat surrogate mother can be determined to be chimeric rats or not, depending on their coat color. 125 Embryos, into which a hChr.21-loxP-EGFP-retaining ES clone (e.g., Rat ES (hChr.21-loxP-EGFP)2, obtained in the above-described Example 2) has been injected, were transplanted into rat surrogate mothers. As a result, 65 chimeric rats (whose coat color had dark brown portions) were bone. Among the 65 chimeric rats, 53 rats were chimeric individuals whose coat could be observed to be colored (FIG. 3). That is to say, it was demonstrated that a rat ES cell line retaining hChr.21-loxP-EGFP had an ability to form chimera, namely, that the rat ES cell line retaining hChr.21-loxP-EGFP had an ability to differentiate into healthy tissues of a rat.

Figure 5:
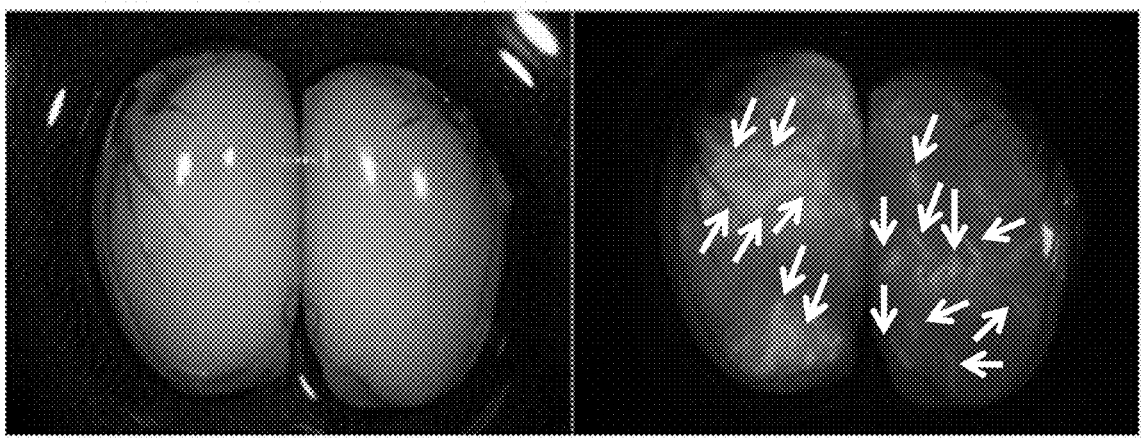
FIG. 5 shows the bright field and GFP fluorescence photographs of the testes of the chimeric rat numbers #1753-2 and #1753-3. It is found that a part of the seminiferous tubule of the rat #1753-2 was GFP-positive (as indicated with arrows).
Figure 5:
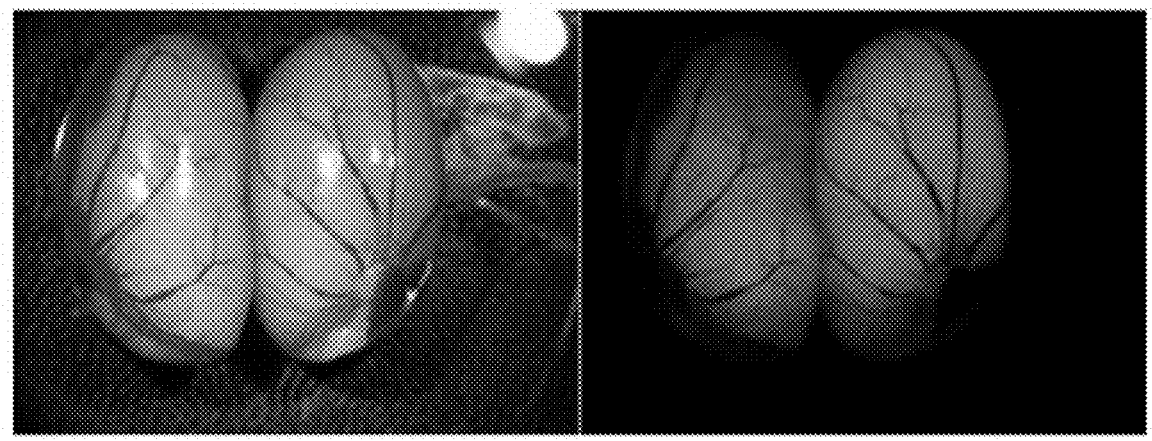

[B] Production of Rats Retaining hChr.21-loxP-EGFP that is Transmitted to Progeny An attempt was made to obtain baby rats by the mating of the above-described chimeric rats; however, GFP-positive rats could not be obtained. Subsequently, since the cause was suggested to be the infertility of trisomic male rats, the GFP-positive rate in the seminiferous tubules was observed and, as a result, one positive rat was observed out of 18 rats (FIG. 4 and FIG. 5). Round spermatids were removed from the GFP-positive seminiferous tubule of the above-described GFP-positive chimeric male rat (Chimeric rat No. #1753-2) (FIG. 5, upper panel). The GFP-positive fraction was sorted by FACS, and was then used in the subsequent experiments.

Figure 6:
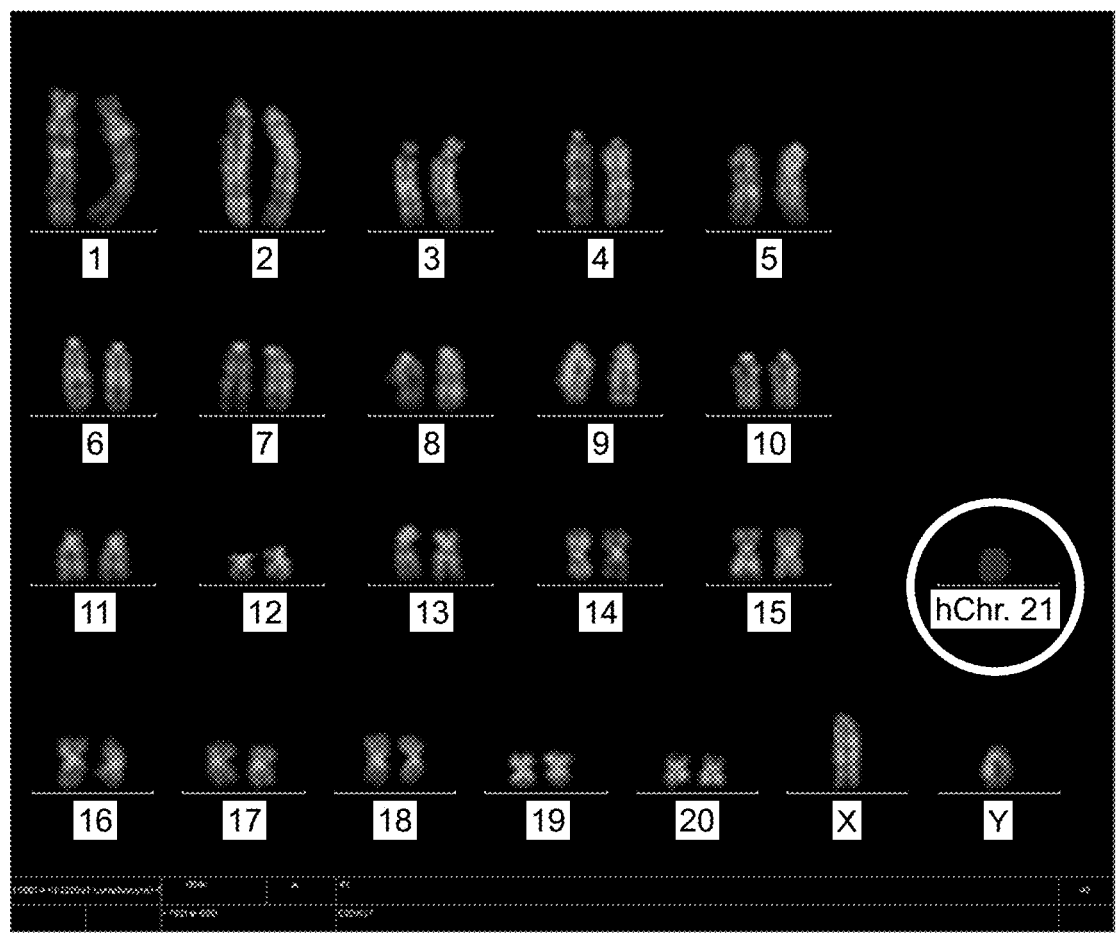
FIG. 6 shows the results of mono-color FISH analysis performed for the cultured blood cells of TC (hChr.21-loxP-EGFP) rat (i.e., the karyotype analysis results), when human Cot-1 DNA was used as a probe. In the figure, hChr.21 indicates human chromosome 21.
Figure 7:
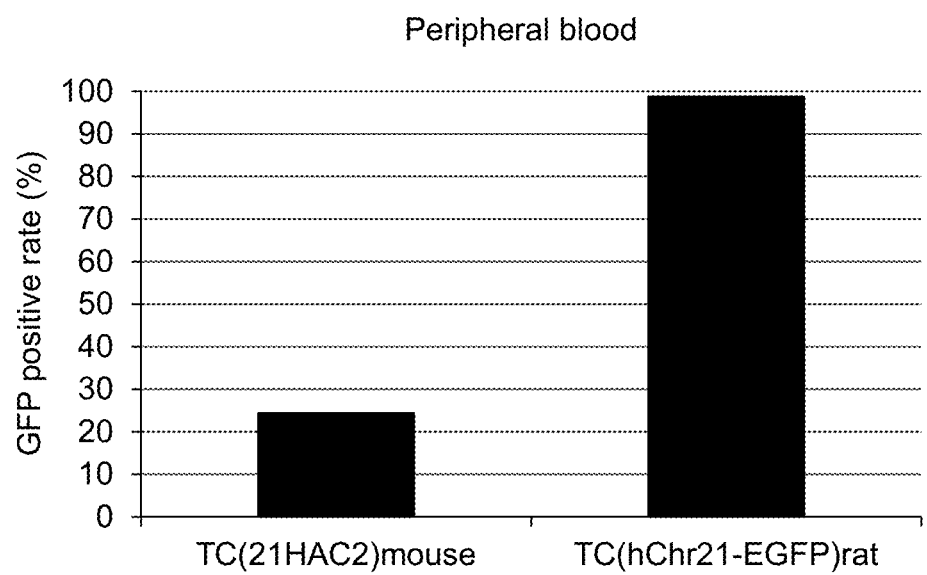
FIG. 7 shows the results of GFP-positive rate (%) of the peripheral bloods of TC (21HAC2) mouse and TC (hChr.21-loxP-EGFP) rat, measured by FCM analysis.

According to the method of Hirabayashi et al. (Exp Anim. 2008 July; 57(4): 401-405), by using the round spermatid injection, GFP-positive round spermatids were injected into the ovum of a rat, and 40 embryos were then transplanted into rat surrogate mothers to produce 13 rats. Among them, 5 rats were GFP-positive. Moreover, 4 out of the 5 rats were found to be positive by PCR performed using the aforementioned primers for detection of the hChr.21-loxP-EGFP region. Thereafter, blood was drawn from the above-described rats, and then, chromosomal specimens after culture were subjected to FISH analysis using human Cot-1 DNA (Tomizuka et al., Nature Genet. 16: 133-143, 1997). As a result, one hChr.21 was specifically detected independently using the above-described probe, and the rat karyotype was normal (FIG. 6). The blood cells in the peripheral blood of the above-described rat were subjected to FCM analysis. As a result, the GFP-positive rate was found to be 98.8%. On the other hand, in the mouse retaining the HAC vector (21HAC2) derived from an EGFP-introduced chromosome 21 described in the document (Kazuki et al., Gene Therapy, 18: 384-393, 2011), the GFP-positive rate was found to be 24.4% (FIG. 7). Specifically, it was demonstrated that a human chromosome (fragment) is instable in the blood cells in the peripheral blood of a mouse, whereas it is stable in the rat. Moreover, using 3 female rats from among the above-described rats, hChr.21-loxP-EGFP-retaining rats were successfully generated by mating. On the other hand, male rats had an extremely small sperm count, and thus, all rats were infertile. From these results, it was concluded that a rat strain retaining hChr.21-loxP-EGFP that is transmittable to progeny could be established. The rat strain, in which hChr.21-loxP-EGFP was transmitted to progeny or offsprings, is referred to as "TC (hChr.21-loxP-EGFP)."

Example 4

Genetic Analysis of TC (hChr.21-loxP-EGFP) Rat

[A] Observation Under Stereoscopic Fluorescence Microscope

Figure 8:
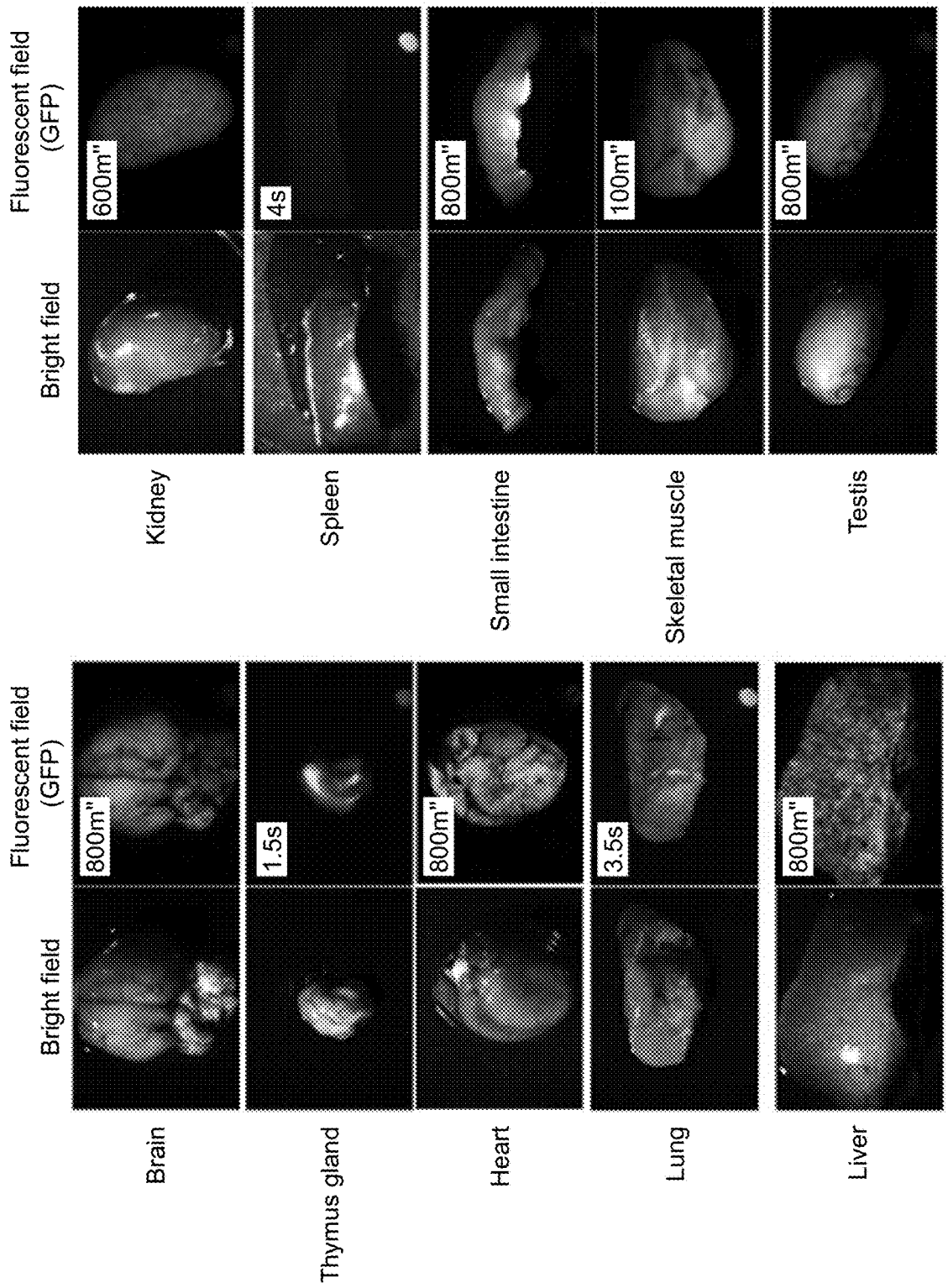
FIG. 8 shows the bright fields and GFP fluorescence fields of each tissue of TC (hChr.21-loxP-EGFP) rats. In each panel of the fluorescence fields, the white shining portion is GFP-positive. The number indicates an exposure time.

The brain, thymus gland, heart, lung, liver, kidney, spleen, small intestine, skeletal muscle and testis of the above-obtained TC (hChr.21-loxP-EGFP) rat were observed under a stereoscopic fluorescence microscope. As a result, all of the tissues were observed to be GFP-positive with the positive rate 100%. The representative results are shown in FIG. 8.

[B] FACS Analysis of Blood Cells

Figure 9:
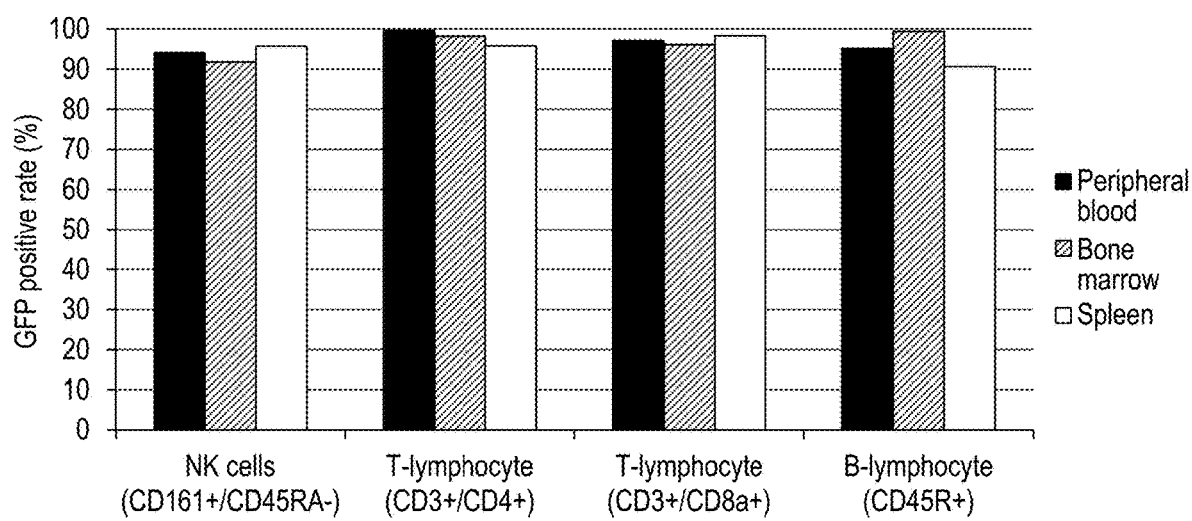
FIG. 9 shows the results of GFP-positive rate (%) of each blood cell lineage in the peripheral blood, bone marrow, and spleen of TC (hChr.21-loxP-EGFP) rat, measured by FACS analysis.

The rat having a GFP-positive rate of 90% or more in the peripheral blood was subjected to FCM analysis using various types of antibodies (BioLegend, ebioscience) specific to blood cell lineage, thereby examining the GFP-positive rate in the blood cell lineage. As a result, the GFP-positive rates in CD61$^+$/CD45RA$^-$ (NK cell-like), CD3$^+$/CD4$^+$ (CD4$^+$ T cells), CD3$^+$/CD8$^+$ (CD8$^+$ T cells), and CD45R$^+$ (B cell-like) were 90% or more in all of the peripheral blood, bone marrow, and spleen. The representative results are shown in FIG. 9.

[C] Fluorescence In Situ Hybridization (FISH) Analysis

Figure 10:
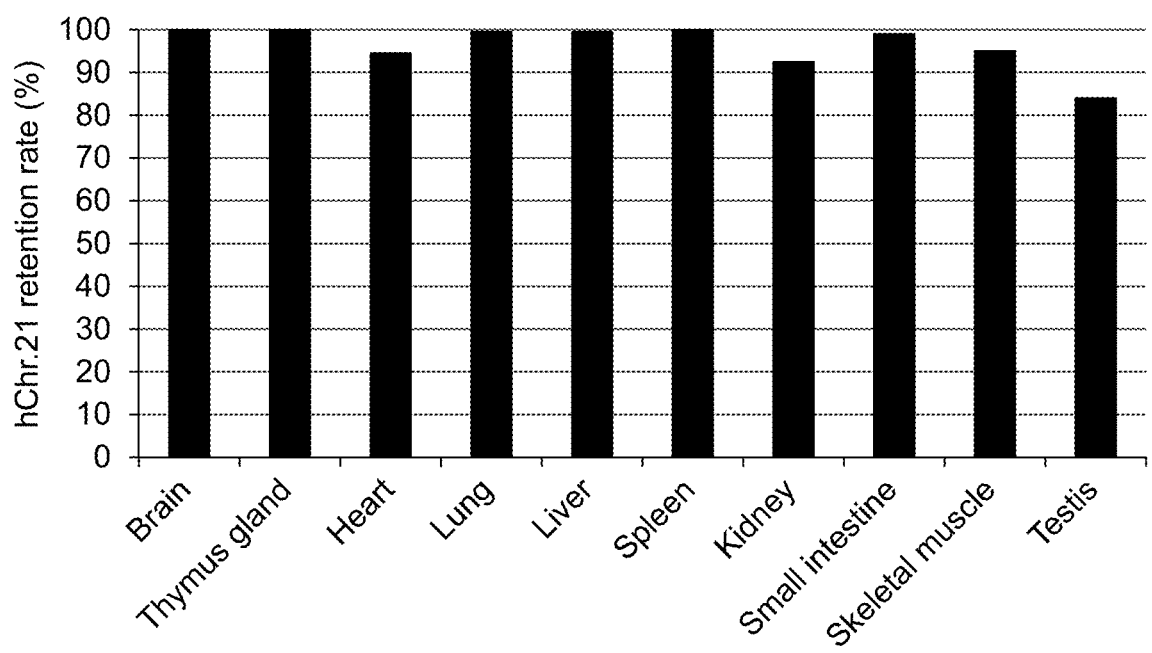
FIG. 10 shows the results of retention rate (%) of human chromosome 21 (hChr.21) in each tissue of TC (hChr.21-loxP-EGFP) rat, measured by FISH analysis, when human Cot-1 DNA was used as a probe.

FISH analysis was carried out on tissues of the rat as described above by the method described by Shinohara et al. (Human Molecular Genetics, 10: 1163-1175, 2001), using Human CotI DNA®(Thermo Fisher Scientific) as a probe. As a result, the presence of hChr.21-loxP-EGFP was visually confirmed, and it was also confirmed that hChr.21-loxP-EGFP was present in 84% to 100% of the cells. The representative results are shown in FIG. 10.

[D] Transmission Rate of TC (hChr.21-loxP-EGFP) Rat Lineage

Female TC (hChr.21-loxP-EGFP) rat was mated with male Crlj:WI rats (white, purchased from Charles River Laboratories, Japan (Yokohama, Kanagawa, Japan), and the transmission rate was examined. From the F2 generation to the F6 generation, 309 baby rats were obtained, and among them, 181 baby rats were GFP-negative, and 128 rats were GFP-positive (transmission rate: 41.4%). That is to say, it was confirmed that the trait of hChr.21-loxP-EGFP appeared at a frequency of 41.4%, although the transmission rate was somewhat lower than the Mendel's law of inheritance (theoretical value: 50%), and thus, it was demonstrated that the Chr.21-loxP-EGFP-retaining rate was 80% or more.

[E] Gene Expression on Human Chromosome 21 in TC (hChr.21-loxP-EGFP) Rat Linage

Total RNA was extracted from the brain, thymus gland, heart, lung, liver, kidney, spleen, small intestine, skeletal muscle and testis of the TC (hChr.21-loxP-EGFP) rat according to commercially available protocols (QIAGEN), and cDNA syntheses were then carried out according to commercially available protocols (Invitrogen). Using the cDNA as a template, PCR was carried out, so that gene expression on the human chromosome 21 was detected. The sequences of the primers are as follows.

Primers for detecting gene expression on human chromosome 21:

APP-L:
(SEQ ID NO: 17)
5'-gccccgtaaaagtgttaca-3'

APP-R:
(SEQ ID NO: 18)
5'-acgtttgtttcttcgtgcct-3'

SOD1-1L:
(SEQ ID NO: 19)
5'-attctgtgatctcactctcagg-3'

SOD1-1R:
(SEQ ID NO: 20)
5'-tcgcgactaacaatcaaagt-3'

IFNAR2-1L:
(SEQ ID NO: 21)
5'-cgaagtttcagtcggtgag-3'

IFNAR2-1R:
(SEQ ID NO: 22)
5'-ggcattcaggttttatccc-3'

TTC3-1L:
(SEQ ID NO: 23)
5'-tggacaaatataaggcatgttca-3'

TTC3-1R:
(SEQ ID NO: 24)
5'-gtcaccttcctctgcctttg-3'

ETS2-1L:
(SEQ ID NO: 25)
5'-taccatgccaatggtttataagg-3'

ETS2-1R:
(SEQ ID NO: 26)
5'-atgtgactgggaacatcttgc-3'

PCP4-1L:
(SEQ ID NO: 27)
5'-gaattcactcatcgtaacttcattt-3'

PCP4-1R:
(SEQ ID NO: 28)
5'-ccttgtaggaaggtatagacaatgg-3'

MX1-1L:
(SEQ ID NO: 29)
5'-tggactgacgacttgagtgc-3'

MX1-1R:
(SEQ ID NO: 30)
5'-ctcatgtgcatctgagggtg-3'

```
-continued
TFF3-1L:
                                         (SEQ ID NO: 31)
5'-ggctgtgattgctgccag-3'

TFF3-1R:
                                         (SEQ ID NO: 32)
5'-gtggagcatgggacctttat-3'

TFF1-1L:
                                         (SEQ ID NO: 33)
5'-cagggatctgcctgcatc-3'

TFF1-1R:
                                         (SEQ ID NO: 34)
5'-atcgatctcttttaatttttaggcc-3'

Primers for detecting expression of control gene:
GAPDH-F:
                                         (SEQ ID NO: 35)
5'-ccatcttccaggagcgaga-3'

GAPDH-R:
                                         (SEQ ID NO: 36)
5'-tgtcataccaggaaatgagc-3'
```

Using GeneAmp9600 manufactured by Perkin-Elmer as a thermal cycler, and also using EX Taq (Takara Bio, Inc., (Kyoto, Japan)) as Taq polymerase, PCR was carried out with the use of a buffer and dNTPs (dATP, dCTP, dGTP, and dTTP) under recommended conditions as mentioned in the attached instruction. With regard to the temperature and cycle conditions, after thermal degeneration at 93° C. for 5 minutes, the reaction was performed for 35 cycles, where one cycle consisted of 93° C.-1 minute, 56° C.-1 minute, and 72° C.-1 minute.

Figure 11:
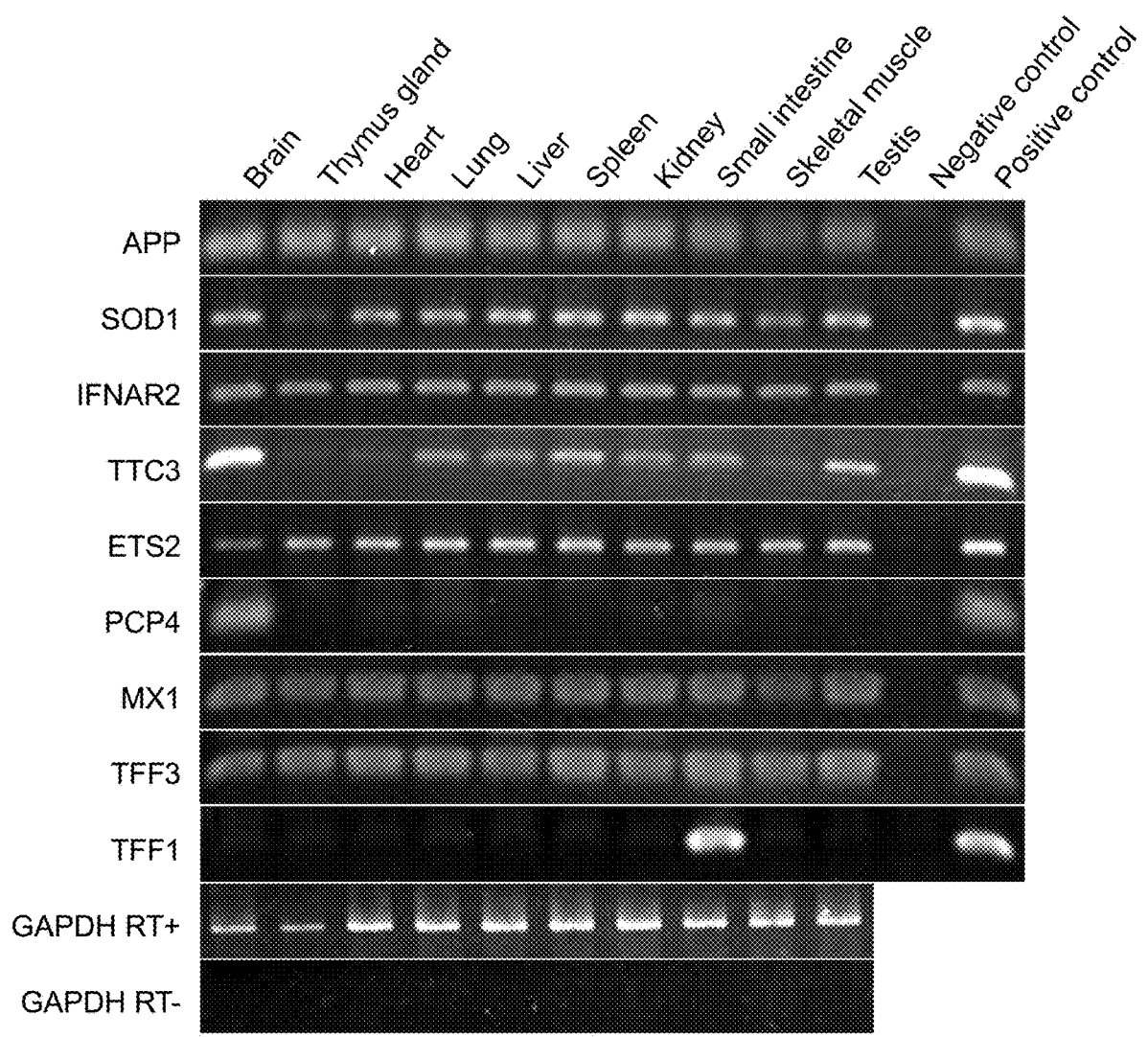
FIG. 11 shows the results of the gene expression analysis of genes on human chromosome 21 in each tissue of TC (hChr.21-loxP-EGFP) rat using RT-PCR method.

As a result, in the TC (hChr.21-loxP-EGFP) rats, PCP4 was detected only in the brain, and TFF1 was detected only in the small intestine. In the case of other primer sets, the expression could be detected in all the examined tissues. In addition, the control GAPDH was detected in all the tissues. The representative results are shown in FIG. 11. As described by Shinohara et al. (HMG, 10: 1163-1175, 2001), genes on the human chromosome 21 were tissue-specifically expressed as in human. Thus, tissue-specific expression, which is also seen in human, was observed.

Example 5

Behavior Analysis of TC (hChr.21-loxP-EGFP) Rats

[A] Light/Dark Transition Test

Using the TC (hChr.21-loxP-EGFP) rat lineage, the GFP-positive rats were used as Down syndrome rat models (hereinafter referred to as "DS"), and GFP-negative rats were used as controls (hereinafter referred to as "Control"). Ten-week-old male rats were prepared (7 animals for each group). In order to reduce stress caused by touching with experimenters, the rats were conditioned to humans (by handling for 5 minutes) when they were 9 weeks old. Using these animals, a light/dark transition test was carried out with reference to the method described in the webpage of RIKEN (http://ja.brc.riken.jp/lab/bpmp/SOPs/index_mc.html).

A light/dark cage for rat (LDK-R, Mel Quest) was equipped into a small animal behavior analysis apparatus SCANET (MV-40, Mel Quest), and then, according to software for small animal behavior analysis system (SCL-40, Mel Quest), the behavior data of the animals in the light/dark cage were obtained. The insensitive zone of SCANET was set at 10. Using a light bulb with daylight color, the light quantity in the center of the light compartment was set at 200 to 213 lux.

Figure 12:
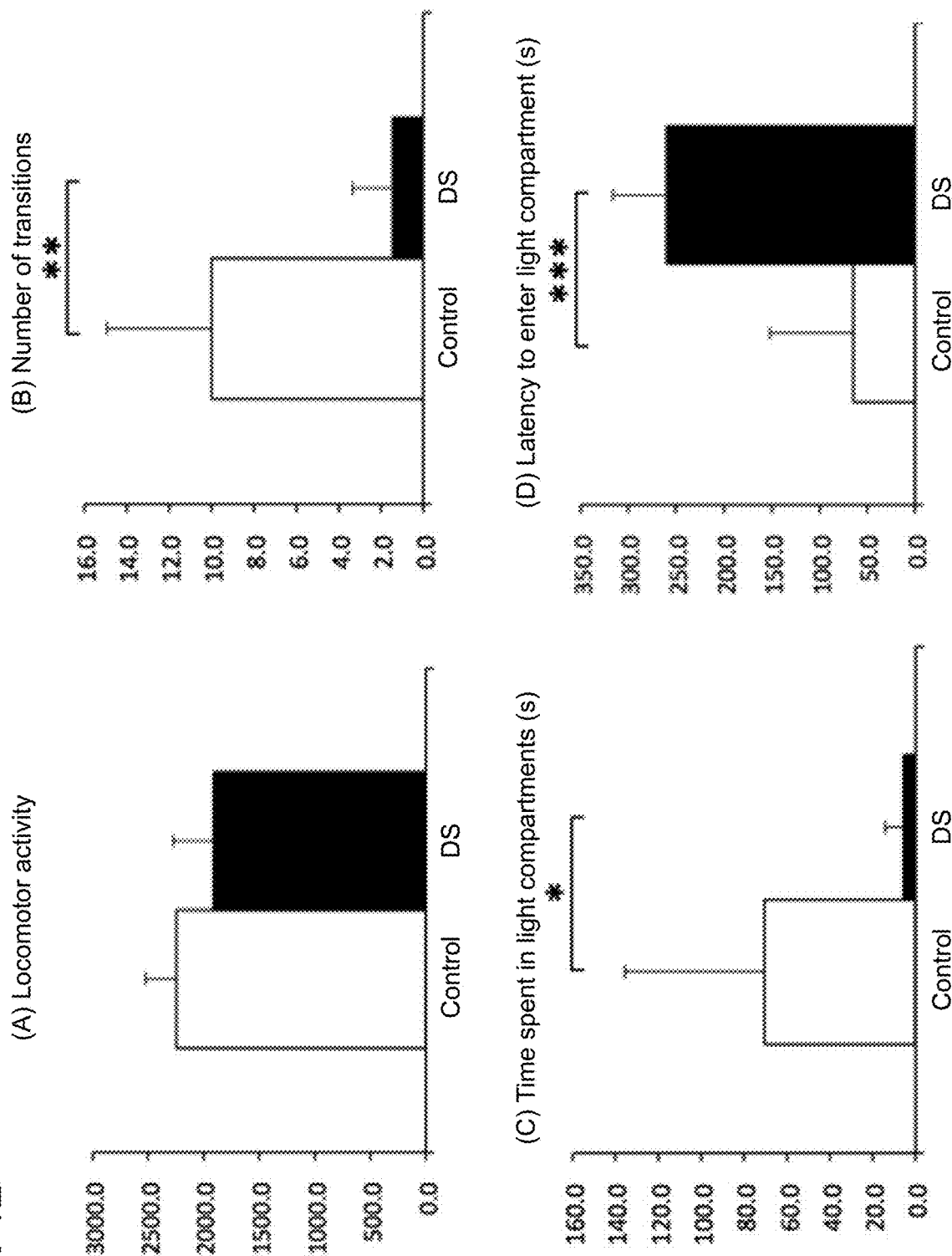
FIG. 12 shows the results of the light/dark transition test (A: locomotor activity (number of passages); B: number of transitions; C: time spent in light compartment (sec); and D: latency to enter light compartment (sec)). In the figure, Control indicates a healthy rat control, and DS indicates the Down syndrome rat model. In addition, the symbols *, , and * indicate $P<0.05$, $P<0.01$, and $P<0.001$, respectively.

In order to condition the animals to a behavior analysis room, the animals were transferred from a breeding room to the behavior analysis room, and after one or more hours had passed, the experiment was started. The animal was placed in a dark compartment in a state that a diaphragm was positioned between a light compartment and a dark compartment, and immediately after the lid was then closed, the diaphragm was removed and the measurement was started. The number of counts proportional to the distance moving during a period of 5 minutes (where the number of counts indicates: locomotor activity=the number of passages through infrared sensors disposed with intervals of 6 mm), the number of comings and goings between light compartment and dark compartment (the number of transitions), the time spent in light compartments, a time required until an animal enters in the light compartment (latency to enter light compartment) were analyzed. As a result, the number of transitions, and the time spent in light compartments were significantly small in DS, and the latency to enter light compartment was significantly large in DS (FIG. 12, Welch's t-test, *P<0.05, P<0.01, *P<0.001). From the above results, it was strongly suggested that anxiety-like behavior be increased in DS.

Figure 13:
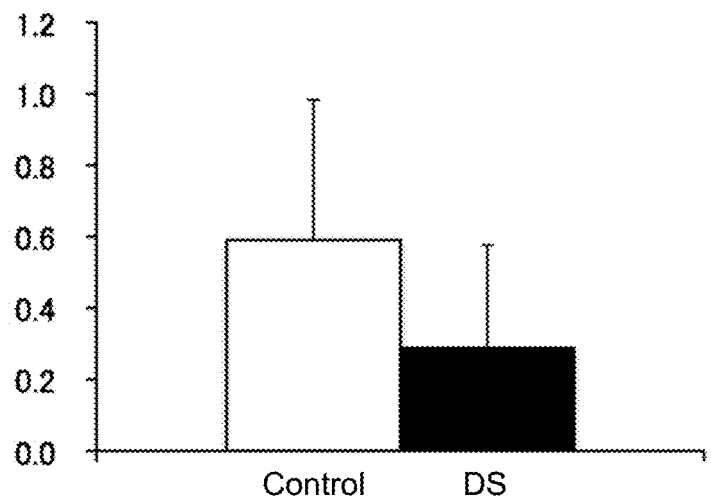
FIG. 13 shows the results of the open field test (the ratio of time spent in center area (sec) to distance traveled (meters)). In the figure, Control is a healthy rat control, and DS indicates the Down syndrome rat model.

[B] Open Field Test 10-week-old male TC (hChr.21-loxP-EGFP) rats were prepared (7 animals for DS, and 7 animals for control group). The rats were conditioned to humans (handling time: 5 minutes), when they were 9 weeks old, and one or more days after termination of the light/dark transition test, an open field test was carried out. The open field test was carried out as follows, with reference to the method described by Kalouda et al. (Pharmacology, Biochemistry and Behavior, 138: 111-116, 2015). In order to condition the animals to a behavior analysis room, the animals were transferred from a breeding room to a behavior analysis room, and, after one or more hours, the experiment was started. The animal was placed into a square-type open field for rat (70 cm×70 cm, Muromachi Kikai Co., Ltd. (Tokyo, Japan)), where the light quantity in the center of the apparatus was set at 30 lux using a light bulb with daylight color, along the wall of the open field from the corner of the same, and the 10-minutes behavior data of the animals were taken using video tracking software (ANY-maze, Stoelting). The time spent in center area (the central area: 30 cm×30 cm) to the distance traveled was analyzed. As a result, the ratio tended to be low in DS (FIG. 13). From the above results, it was demonstrated that anxiety-like behavior was increased in DS.

[C] Elevated Plus Maze Test 10-week-old male TC (hChr.21-loxP-EGFP) rats were prepared (6 animals for DS, and 6 animals for control group). The rats were conditioned to humans (handling time: 5 minutes), when they were 9 weeks old, and thereafter, the animals used in the light/dark transition test and the open field test were also used in the elevated plus maze test.

Figure 14:
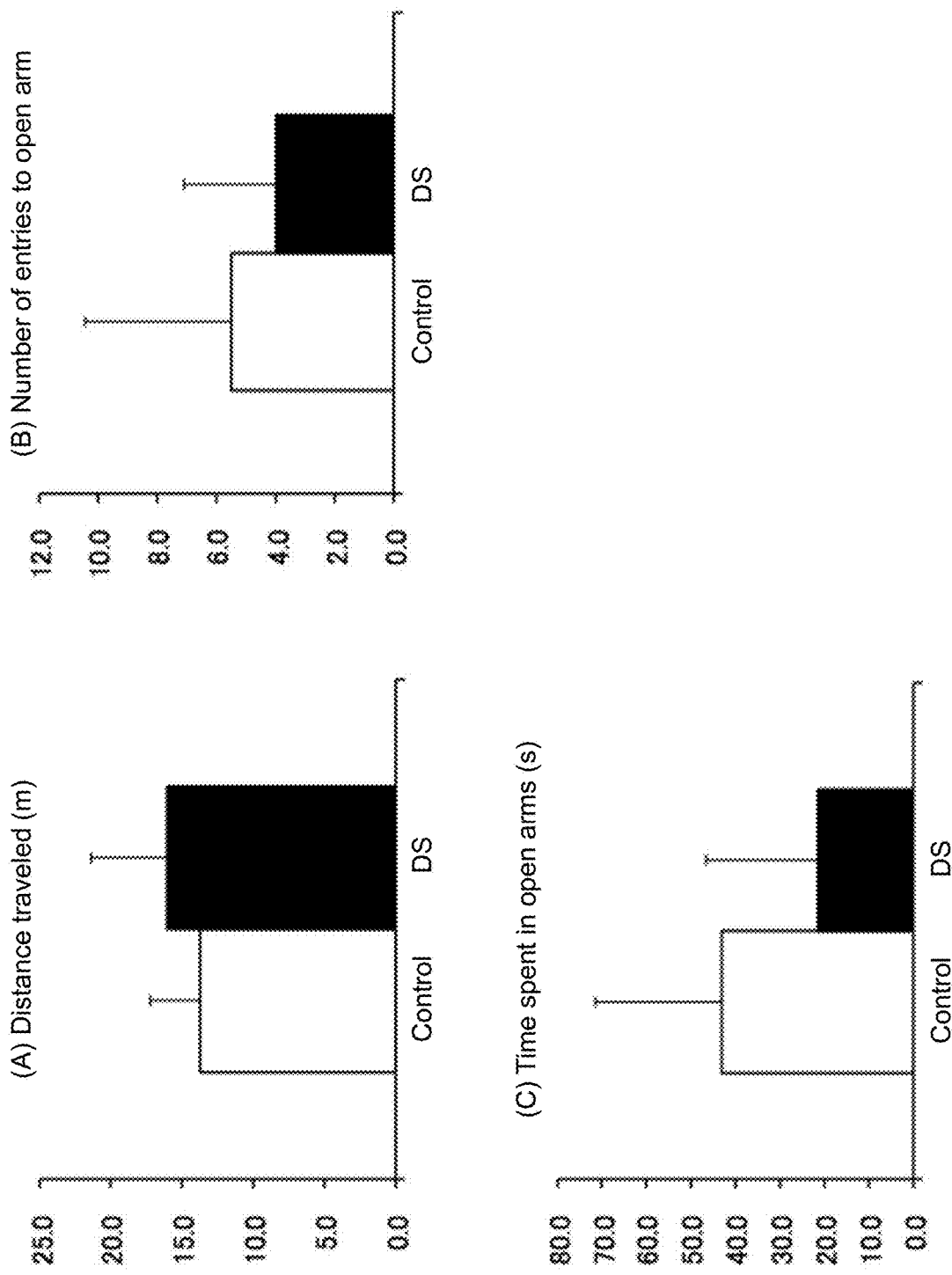
FIG. 14 shows the results of the elevated plus maze test (A: distance traveled (meters), B: number of entries to open arm; and C: time spent in open arm (sec)). In the figure, Control is a healthy rat control, and DS indicates the Down syndrome rat model.

With reference to the methods described by Glombik et al. and Aydin et al. (Molecular Neurobiology, DOI 10.1007/s 12035-016-9807-4, 2016, Molecular Neurobiology, DOI 10.1007/s12035-016-9693-9, 2016), the elevated plus maze test was carried out as follows. In order to condition the animals to a behavior analysis room, the animals were transferred from a breeding room to a behavior analysis room, and after one or more hours, the experiment was started. An elevated plus maze for rat, in which the light quantity in the center of the apparatus was set at 39 to 42 lux using a light bulb with daylight color (arm width: 10 cm, arm length: 50 cm, arm height: 40 cm, neutral zone: 10 cm×10 cm, Muromachi Kikai Co., Ltd.) was prepared. The animal was placed on the neutral zone, where the head of the animal was directed towards the closed arm, and the 5-minutes behavior data of the animal were taken using video tracking software (ANY-maze, Stoelting). The distance traveled (meters), the number of entries to open arm, and the time spent in open arm (sec) were analyzed. As a result, the time spent in open arm tended to be low in DS (FIG. 14). From the above results, it was demonstrated that anxiety-like behavior was increased in DS.

INDUSTRIAL APPLICABILITY

The Down syndrome rat model of the present invention can transmit a human chromosome 21 or fragment thereof or an exogenous rat chromosome or fragment thereof to offsprings, and the rat model also has the symptoms of Down syndrome (abnormal behavior, etc.). Thus, using the Down syndrome rat model of the invention, sophisticated cognitive function tests can be carried out. As such, the Down syndrome rat model is industrially useful as a model for the development of therapeutic agents or elucidation of the pathogenic mechanism.

All publications, patents, and patent applications cited herein are incorporated herein by reference in their entirety.

The invention claimed is:

1. A genetically modified rat that models Down Syndrome, wherein at least 80% of tissues in the rat comprise a full length human chromosome 21, and the rat exhibits symptoms of Down Syndrome.

2. The genetically modified rat that models Down Syndrome of claim 1, wherein the human chromosome 21 comprises DNA encoding a fluorescent protein.

3. A method for producing a genetically modified rat that models Down syndrome, the method comprising:
   a) fusing a microcell comprising a full-length human chromosome 21 with a male embryonic stem (ES) cell such that a chimeric ES cell comprising the full-length human chromosome 21 is obtained;
   b) introducing the chimeric ES cells obtained in step a) into a rat blastocyst or 8-cell embryo such that a chimeric embryo is obtained,
   c) transplanting the chimeric embryo obtained in step b) into a recipient female rat such that a chimeric male rat is obtained;
   d) inseminating a female rat with spermatids obtained from the chimeric male rat to produce a plurality of rat progeny; and
   e) selecting the genetically modified rat of claim 2 from the plurality of rat progeny produced in step (d).

4. The method according to claim 3, wherein the human chromosome 21 comprises DNA encoding a fluorescent protein.

* * * * *

```
                          SEQUENCE LISTING

<160> NUMBER OF SEQ ID NOS: 36

<210> SEQ ID NO 1
<211> LENGTH: 28
<212> TYPE: DNA
<213> ORGANISM: Artificial
<220> FEATURE:
<223> OTHER INFORMATION: primer

<400> SEQUENCE: 1
aaatgcatca ccattctccc agttaccc                                          28

<210> SEQ ID NO 2
<211> LENGTH: 22
<212> TYPE: DNA
<213> ORGANISM: Artificial
<220> FEATURE:
<223> OTHER INFORMATION: primer

<400> SEQUENCE: 2
ggagatgagg aagaggagaa ca                                                22

<210> SEQ ID NO 3
<211> LENGTH: 23
<212> TYPE: DNA
<213> ORGANISM: Artificial
<220> FEATURE:
<223> OTHER INFORMATION: primer

<400> SEQUENCE: 3
gggtaagaag gtgcttaatg ctc                                               23

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
tgaatatggg ttctggatgt agtg                                              24

<210> SEQ ID NO 5
<211> LENGTH: 35
<212> TYPE: DNA
<213> ORGANISM: Artificial
<220> FEATURE:
<223> OTHER INFORMATION: primer

<400> SEQUENCE: 5 gaggggact gggacaagcc ctttgctgga agaga                                   35

<210> SEQ ID NO 6
```

```
<211> LENGTH: 35
<212> TYPE: DNA
<213> ORGANISM: Artificial
<220> FEATURE:
<223> OTHER INFORMATION: primer

<400> SEQUENCE: 6
acattaggaa aaatcaaaag gtccaattat taagg                              35

<210> SEQ ID NO 7
<211> LENGTH: 20
<212> TYPE: DNA
<213> ORGANISM: Artificial
<220> FEATURE:
<223> OTHER INFORMATION: primer

<400> SEQUENCE: 7
caacagagtg agacaggctc                                               20

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
ttccaggaac cactacactg                                               20

<210> SEQ ID NO 9
<211> LENGTH: 35
<212> TYPE: DNA
<213> ORGANISM: Artificial
<220> FEATURE:
<223> OTHER INFORMATION: primer

<400> SEQUENCE: 9
ggcttgggga cattgagtca tcacaatgta gatgt                              35

<210> SEQ ID NO 10
<211> LENGTH: 35
<212> TYPE: DNA
<213> ORGANISM: Artificial
<220> FEATURE:
<223> OTHER INFORMATION: primer

<400> SEQUENCE: 10
gaagaaaggc aaatgaagac ctgaacatgt aagtt                              35

<210> SEQ ID NO 11
<211> LENGTH: 25
<212> TYPE: DNA
<213> ORGANISM: Artificial
<220> FEATURE:
<223> OTHER INFORMATION: primer

<400> SEQUENCE: 11
gggactgtaa taaatattct gttgg                                         25

<210> SEQ ID NO 12
<211> LENGTH: 17
<212> TYPE: DNA
<213> ORGANISM: Artificial
<220> FEATURE:
<223> OTHER INFORMATION: primer

<400> SEQUENCE: 12
```

```
cactggctct cctgacc                                                17
```

<210> SEQ ID NO 13
<211> LENGTH: 18
<212> TYPE: DNA
<213> ORGANISM: Artificial
<220> FEATURE:
<223> OTHER INFORMATION: primer

<400> SEQUENCE: 13

```
gatcctcctg aatgcctg                                               18
```

<210> SEQ ID NO 14
<211> LENGTH: 18
<212> TYPE: DNA
<213> ORGANISM: Artificial
<220> FEATURE:
<223> OTHER INFORMATION: primer

<400> SEQUENCE: 14

```
gtaaatgccc tttggacc                                               18
```

<210> SEQ ID NO 15
<211> LENGTH: 22
<212> TYPE: DNA
<213> ORGANISM: Artificial
<220> FEATURE:
<223> OTHER INFORMATION: primer

<400> SEQUENCE: 15

```
tggaggccat aaacaagaag ac                                          22
```

<210> SEQ ID NO 16
<211> LENGTH: 21
<212> TYPE: DNA
<213> ORGANISM: Artificial
<220> FEATURE:
<223> OTHER INFORMATION: primer

<400> SEQUENCE: 16

```
ccccttgacc cagaaattcc a                                           21
```

<210> SEQ ID NO 17
<211> LENGTH: 19
<212> TYPE: DNA
<213> ORGANISM: Artificial
<220> FEATURE:
<223> OTHER INFORMATION: primer

<400> SEQUENCE: 17

```
gccccgtaaa agtgttaca                                              19
```

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18

```
acgtttgttt cttcgtgcct                                             20
```

<210> SEQ ID NO 19
<211> LENGTH: 22
<212> TYPE: DNA

```
<213> ORGANISM: Artificial
<220> FEATURE:
<223> OTHER INFORMATION: primer

<400> SEQUENCE: 19
attctgtgat ctcactctca gg                                      22

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
tcgcgactaa caatcaaagt                                         20

<210> SEQ ID NO 21
<211> LENGTH: 19
<212> TYPE: DNA
<213> ORGANISM: Artificial
<220> FEATURE:
<223> OTHER INFORMATION: primer

<400> SEQUENCE: 21
cgaagtttca gtcggtgag                                          19

<210> SEQ ID NO 22
<211> LENGTH: 19
<212> TYPE: DNA
<213> ORGANISM: Artificial
<220> FEATURE:
<223> OTHER INFORMATION: primer

<400> SEQUENCE: 22
ggcattcagg ttttatccc                                          19

<210> SEQ ID NO 23
<211> LENGTH: 23
<212> TYPE: DNA
<213> ORGANISM: Artificial
<220> FEATURE:
<223> OTHER INFORMATION: primer

<400> SEQUENCE: 23
tggacaaata taaggcatgt tca                                     23

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
gtcaccttcc tctgcctttg                                         20

<210> SEQ ID NO 25
<211> LENGTH: 23
<212> TYPE: DNA
<213> ORGANISM: Artificial
<220> FEATURE:
<223> OTHER INFORMATION: primer

<400> SEQUENCE: 25
taccatgcca atggtttata agg                                     23
```

```
<210> SEQ ID NO 26
<211> LENGTH: 21
<212> TYPE: DNA
<213> ORGANISM: Artificial
<220> FEATURE:
<223> OTHER INFORMATION: primer

<400> SEQUENCE: 26
atgtgactgg gaacatcttg c                                              21

<210> SEQ ID NO 27
<211> LENGTH: 25
<212> TYPE: DNA
<213> ORGANISM: Artificial
<220> FEATURE:
<223> OTHER INFORMATION: primer

<400> SEQUENCE: 27
gaattcactc atcgtaactt cattt                                          25

<210> SEQ ID NO 28
<211> LENGTH: 25
<212> TYPE: DNA
<213> ORGANISM: Artificial
<220> FEATURE:
<223> OTHER INFORMATION: primer

<400> SEQUENCE: 28
ccttgtagga aggtatagac aatgg                                          25

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
tggactgacg acttgagtgc                                                20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
ctcatgtgca tctgagggtg                                                20

<210> SEQ ID NO 31
<211> LENGTH: 18
<212> TYPE: DNA
<213> ORGANISM: Artificial
<220> FEATURE:
<223> OTHER INFORMATION: primer

<400> SEQUENCE: 31
ggctgtgatt gctgccag                                                  18

<210> SEQ ID NO 32
<211> LENGTH: 20
<212> TYPE: DNA
<213> ORGANISM: Artificial
<220> FEATURE:
```

```
<223> OTHER INFORMATION: primer

<400> SEQUENCE: 32
gtggagcatg ggacctttat                                              20

<210> SEQ ID NO 33
<211> LENGTH: 18
<212> TYPE: DNA
<213> ORGANISM: Artificial
<220> FEATURE:
<223> OTHER INFORMATION: primer

<400> SEQUENCE: 33
cagggatctg cctgcatc                                                18

<210> SEQ ID NO 34
<211> LENGTH: 25
<212> TYPE: DNA
<213> ORGANISM: Artificial
<220> FEATURE:
<223> OTHER INFORMATION: primer

<400> SEQUENCE: 34
atcgatctct tttaattttt aggcc                                        25

<210> SEQ ID NO 35
<211> LENGTH: 19
<212> TYPE: DNA
<213> ORGANISM: Artificial
<220> FEATURE:
<223> OTHER INFORMATION: primer

<400> SEQUENCE: 35
ccatcttcca ggagcgaga                                               19

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
tgtcatacca ggaaatgagc                                              20
```